US006569353B1

(12) United States Patent
Giletto et al.

(10) Patent No.: US 6,569,353 B1
(45) Date of Patent: *May 27, 2003

(54) REACTIVE DECONTAMINATION FORMULATION

(75) Inventors: Anthony Giletto, College Station, TX (US); William White, College Station, TX (US); Alan J. Cisar, Cypress, TX (US); G. Duncan Hitchens, Bryan, TX (US); James Fyffe, Bryan, TX (US)

(73) Assignee: Lynntech, Inc., College Station, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/096,435

(22) Filed: Jun. 11, 1998

(51) Int. Cl.$^7$ ............................................... C09K 3/00
(52) U.S. Cl. ........................... 252/186.28; 252/186.38; 252/186.33; 422/28; 424/646; 424/648; 424/616
(58) Field of Search ................. 252/186.28, 186.38, 252/186.33; 422/28; 424/646, 648, 616; 210/759

(56) References Cited

U.S. PATENT DOCUMENTS

| | | | | |
|---|---|---|---|---|
| 2,933,453 A | * | 4/1960 | Burks .................... | 252/186.29 |
| 4,017,411 A | * | 4/1977 | Diehl et al. ............ | 252/186.29 |
| 4,021,361 A | | 5/1977 | Lee .......................... | 252/102 |
| 4,051,058 A | | 9/1977 | Bowing ..................... | 252/186 |
| 4,130,501 A | | 12/1978 | Lutz .......................... | 252/186 |
| 4,216,041 A | | 8/1980 | Dearfdorff .................. | 149/44 |
| 4,370,241 A | * | 1/1983 | Junkermann et al. ....... | 210/759 |
| 4,430,236 A | | 2/1984 | Franks ....................... | 252/95 |
| 4,496,473 A | | 1/1985 | Sanderson ............. | 252/186.41 |
| 4,574,714 A | | 3/1986 | Bach ......................... | 110/346 |
| 4,612,404 A | | 9/1986 | Thyagarajan ............. | 568/730 |
| 4,772,290 A | | 9/1988 | Mitchell ....................... | 8/107 |
| 4,850,729 A | * | 7/1989 | Kramer et al. ............ | 401/183 |
| 4,902,441 A | * | 2/1990 | Pellenbarg et al. ..... | 252/187.26 |
| 4,927,627 A | | 5/1990 | Schrader ..................... | 424/62 |
| 4,941,989 A | | 7/1990 | Kramer et al. ............. | 252/102 |
| 5,008,106 A | | 4/1991 | Merianos .................... | 424/80 |
| 5,032,178 A | * | 7/1991 | Cornell ........................ | 106/35 |
| 5,393,305 A | | 2/1995 | Cohen .......................... | 8/406 |
| 5,508,046 A | | 4/1996 | Cosentino .................. | 424/616 |
| 5,531,963 A | | 7/1996 | Powell ....................... | 422/30 |
| 5,545,799 A | | 8/1996 | Ritter ......................... | 588/200 |
| 5,580,485 A | * | 12/1996 | Feringa et al. ............. | 510/311 |
| 5,656,302 A | | 8/1997 | Cosentino .................. | 424/616 |
| 5,681,805 A | | 10/1997 | Scheuing .................... | 510/277 |
| 5,688,851 A | | 11/1997 | Kress ........................ | 138/141 |
| 5,689,038 A | | 11/1997 | Bartram ..................... | 588/200 |
| 5,710,358 A | * | 1/1998 | Yang et al. ................. | 588/200 |
| 5,720,983 A | | 2/1998 | Malone ...................... | 424/616 |

OTHER PUBLICATIONS

N. Uri, *Inorganic Free Radical In Solution*; Chemistry Department, University of Manchester, Manchester 13, Great Britain; Received Sep. 20, 1951; pp. 375, 400–407 and 452.

Cheves Walling & Shin'ichi Kato, The Oxidation of Alcohols by Fenton's Reagent, The Effect of Copper Ion[1]; The Journal of the American Chemical Society/93:17/Aug. 25, 1971; Contribution from the Department of Chemistry, University of Utah, Salt Lake City, Utah 84112. Rec'd Nov. 3, 1970.

Cheves Walling, *Fenton's Reagent Revisited*; vol. 8, 1975; Department of Chemistry, University of Utah, Salt Lake City, Utah 84112; Received Aug. 30, 1974.

I.M. Kolthoff & A. I. Medallia, "The Reaction between Ferrous Iron and Peroxides; I. Reaction with Hydrogen Peroxide in the Absence of Oxygen[1]"; Reaction of Ferrous Iron with Hydrogen Peroxide in Absence of Oxygen; Nov., 1949; vol. 71; pp. 3777–3783.

Peter Wardman & Luis P. Caneias; "Fenton Centennial Symposium; Fenton Chemistry; An Introduction[1]"; Radiation Research 145, 523–531 (1996).

Kerem Z, Jensen KA, Hammel KE, "Biodegradative mechanism of the brown rot basidiomycete *Gloeophyllum trabeum*: evidence for an extracellular hydroquinone–driven fenton reaction"; FEBS LETTERS, 446 (1):49–54, Mar. 5, 1999.

Prousek J, Duriskova I, "Oxidative degradation of poly(ethylene glycol)s (PEG) by the Fenton and photo–Fenton reactions"; CHEMICKE LISTY 92 (3):218–220, 1998.

Kenneth A. Jensen, Jr., Carl J Houtman, Zachary C. Ryan, Kenneth E. Hammel, "Pathways for the Extracellular Fenton Chemistry in the Brown Rot Basidiomycete *Gloeophyllum trabeum*"; Applied and Environmental Microbiology, Jun. 2001, pp. 2705–2711; vol. 67, No. 6.

M. Kitis, C. D. Adams, & G. T. Daigger; "The Effects of Fenton's Reagent Pretreatment on the Biodegradability of Nonionic Surfactants"; *Wat. Res.* vol. 33, No. 11, pp. 2561–2568, 1999.

(List continued on next page.)

*Primary Examiner*—Robert J. Warden, Sr.
*Assistant Examiner*—LaToya Cross
(74) *Attorney, Agent, or Firm*—Streets & Steele; Jeffrey L. Streets

(57) ABSTRACT

The present invention provides a universal decontamination formulation and method for detoxifying chemical warfare agents (CWA's) and biological warfare agents (BWA's) without producing any toxic by-products, as well as, decontaminating surfaces that have come into contact with these agents. The formulation includes a sorbent material or gel, a peroxide source, a peroxide activator, and a compound containing a mixture of $KHSO_5$, $KHSO_4$ and $K_2SO_4$. The formulation is self-decontaminating and once dried can easily be wiped from the surface being decontaminated. A method for decontaminating a surface exposed to chemical or biological agents is also disclosed.

174 Claims, 5 Drawing Sheets

OTHER PUBLICATIONS

Sheng H. Lin, Chi M. Lin & Horing G. Leu, "Operating Characteristics and Kinetic Studies of Surfactant Wastewater Treatment by Fenton Oxidation"; *Wat. Res.* vol. 33, No. 7, pp. 1735–1741, 1999.

F. Ferrero, "Oxidative degradation of dyes and surfactant in the Fenton and photo–Fenton treatment of dyehouse effluents"; JSDC vol. 116, May/Jun. 2000; pp. 148–153.

Daniel M. Larking, Russell, J. Crawford, Gregor B. Y. Christie & Greg T. Lonergan; "Enhanced Degradation of Polyvinyl Alcohol by *Pycnoporus cinnabarinus* after Pretreatment with Fenton's Reagent"; Applied and Environmental Microbiology, Apr. 1999, pp. 1798–1800. vol. 65, No. 4.

Lecheng Lei, Xijun Hu, Po Lock Yue, Stefan H. Bossmann, Sabine Gob & Andre' M. Braun, "Oxidative degradation of polyvinyl alcohol by the photochemically enhanced Fenton reaction"; Journal of Photochemistry and Photobiology A: Chemistry 116 (1998); pp. 159–166.

Stefan H. Bossmann, Esther Oliveros, Sabine Gob, Mark Kantor, Alexander Goppert, Andre M. Braun, Lecheng Lei & Po Lock Yue, "Oxidative Degradation of Polyvinyl Alchohol by the Photochemically Enhanced Fenton Reaction. Evidence for the Formation of Super–Macromolecules"; Progress in Reaction Kinetics and Mechanism, vol. 26, pp. 113–137, 20C.

Chemical Warfare Agents, An overview of chemicals defined as chemical weapons, Jul. 18, 1996.

Nerve Agents, Lethal organo–phosphorus compounds inhibiting cholinesterase, Aug. 2, 1996.

CW Protective Equipment, An overview of respiratory and body protection, Mar. 21, 1996.

Protection against Chemical Weapons, An introduction, Aug. 2, 1996.

Decontamination of Chemical Warfare Agents, an introduction to methods and chemicals for decontamination, Mar. 21, 1996.

Toxins, Potential Chemical Weapons from living organisms, Aug. 2, 1996.

Mustard Agents, An overview of the sulfur and nitrogen mustard agents, Mar. 15, 1996.

Collective CW Protection, An overview of methods for collective protection against chemical weapons, Mar. 21, 1996.

Detection of Chemical Weapons, An overview of methods for the detection of chemical warfare agents, Mar. 21, 1996.

M48/M49 Chemical–Biological Aircraft Mast.

Decontamination Kit, Individual Equipment: M295.

M41 Protection Assessment Test System (PATS).

Dispersal of Chemical Warfare Agents, Influence of weather, terrain, and buildings, Apr. 29, 1997.

Mechanism of enhanced TXE and PCP Biodegradation Following Pre– Oxidation, May 1994.

Fenton's Reagent, Iron–Catalyzed Hydrogen Peroxide.

Introduction to Hydrogen Peroxide, Environmental Application Overview.

Yu–Chu Yang, James A. Baker and J. Richard Ward, Decontamination of Chemical Warfare Agents, 1992, p 1729–1743.

G.B. Wickramanayake, Disinfection and Sterilization By Ozone, Chapter 10, p 182–190. 1991.

* cited by examiner

REACTIVE DECONTAMINATION FORMULATION

This invention was made with government support under grant DE-FG03-97ER82420 awarded by the Department of Energy. The government has certain rights in this invention.

BACKGROUND OF THE INVENTION

1. Field of the Invention

This invention relates to a formulation for decontaminating a variety of toxic agents.

2. Background of the Related Art

Over many years, various highly toxic chemical and biological warfare agents have been developed and stockpiled by several nations. These weapons are very efficient in causing multiple casualties and cannot easily be detected, making their production and eventual deployment difficult to monitor. In addition, these weapons cost relatively little to produce and are easy to manufacture. In view of the hazards associated with these agents, it is essential to have formulations which can rapidly and efficiently decontaminate surfaces which have been exposed to these chemical and biological warfare agents.

An important aspect of any containment strategy is to be able to neutralize the threat using chemical decontamination methods. Most chemical warfare agents (CWA's) and biological warfare agents (BWA's) can be destroyed or rendered harmless by suitable chemical treatments. Unfortunately, existing chemical treatments for neutralization of biological and chemical agents have significant drawbacks. A "universal" formulation that can decontaminate all biological and chemical threats is not available. Existing decontamination solutions are only effective against a certain class of agents. In order to be effective, emergency response personnel would need several types of decontaminants available on-hand. Use of existing decontaminants under inappropriate conditions can result in the formation of dangerous by-products. For example, a dilute bleach solution is very effective at destroying anthrax spores, but an extremely toxic by-product is formed if used to destroy VX. Furthermore, some chemicals, such as sodium hydroxide dissolved in organic solvents are unsuitable for use in certain conditions because they corrode, etch or erode materials.

Today, many different types of CWA's and BWA's are known. The CWA's fall into three main classes: sulfer mustards (HD), nitrogen mustards ($HN_3$), and organophosphorous nerve agents (acetylcholinesterase inhibitors) of the G (GA, GB, GD, GE, GF) and V (VX, VE, VG, VM) type. BWA's can be classified into at least five categories: viruses, bacteria, rickettsia, biological toxins, and genetically engineered agents.

Most decontamination processes include some form of hydrolysis. Hydrolysis of CWA's creates intermediates or oxidation by-products of organophosphorous compounds that are sometimes more toxic than the agent itself. While hydrolysis may be acceptable for many organophosphorous compounds, it is not universally effective against all of these compounds and great care must be taken to first identify then treat the agent under the proper hydrolyzing conditions.

The oxidation of neutral organo-phosphorous esters (OPEs) usually involves atoms other than phosphorus. In compounds containing sulfur, oxidation generally occurs at the sulfur atom In unprotected nitrogen moieties, oxidation at nitrogen will occur and may result in increased inhibition of acetylcholine esterase. From a toxicological standpoint, random oxidation of organophosphorous compounds at critical sites could result in the production of better esterase inhibitors.

These considerations highlight the need for a system capable of decontaminating a broad range of chemical and biological agents without producing toxic by-products. In addition, there is a need for a decontamination system that is compatible with most common materials, easy to dispense and environmentally safe.

SUMMARY OF THE INVENTION

The present invention provides for a formulation for decontaminating toxic agents such as chemical and biological warfare agents and pesticides. The formulation comprises a sorbent containing $HSO_5^-$ ions, an oxidant, and an activator dispersed in the oxidant for activating the oxidant. Preferably, the compound containing $HSO_5^-$ ions is selected from potassium monopersulfate, sodium monopersulfate, ammonium monopersulfate, $HSO_5^-$ salts of other alkali metals, and $HSO_5^-$ salts of alkaline earth metals, most preferably having, formula $2KHSO_5 \cdot KHSO_4 \cdot K_2SO_4$, which is commercially available as OXONE.

The oxidant can be selected from perborates, persulfates, organic peroxides, alkali metal peroxides, alkali metal superoxides, and alkaline earth metal peroxides, preferably hydrogen peroxide. There are a number of known activators for peroxide oxidation reactions. Some useful activators include iron salts, as well as the salts of copper, titanium, chromium, vanadium, zinc, cobalt, and nickel. Finely divided metals capable of being readily oxidized to form metal cations are considered to be within the scope of this invention. Preferably, the activator is in the form of ferrous ions. In addition, phosphate ions may also be used in the formulation to control the temperature of the reaction.

The sorbent material may be selected from silicon dioxide, silica gel, silicon oxyhydroxides, aluminum oxide, alumina gel, aluminum oxyhydroxides, aluminates, other metal oxides, other metal oxyhydroxides, clay minerals and mixtures thereof, preferably, fumed silica. The ideal sorbent is inert and has a high surface area and capacity for absorbing or adsorbing the contaminants.

The $HSO_5^-$ ion concentration can range from about 0.05M to about 0.5M, preferably from about 0.1M to about 0.3M. The oxidant concentration can range from about 0.5M to about 5M, preferably from about 0.5M— to about 1.5M. The activator concentration can range from about 0.05M to about 0.5M, preferably from about 0.1M to about 0.3M. The final sorbent material concentration may be from about 3% to about 20% by weight, preferably from about 5% to about 15% by weight.

A system for decontaminating toxic agents is also provided. The system comprises an $HSO_5^-$ ion, an oxidant capable of forming free hydroxyl radicals, a metal catalyst or activator dispersed within the oxidant, and a sorbent material, wherein the $HSO_5^-$ ions, the oxidant and the metal catalyst are dispersed within the sorbent material. Preferably, a dispenser is provided with a first compartment for holding the $HSO_5^-$ ions and the oxidant dispersed in the sorbent material and a second compartment for holding the metal catalyst or activator dispersed in the sorbent material. The dispenser may also have a nozzle with a mixer for mixing the $HSO_5^-$ ions and oxidant with the metal catalyst or activator. The sorbent compounds containing $HSO_5^-$ ions, the oxidant, and the metal catalyst are described above. Preferably, the ratio of oxidant to $HSO_5^-$ ion is 90:10.

In another embodiment of the present invention, there is provided a method for decontaminating a toxic agent disposed on a surface. The method includes reacting the toxic agent with a sufficient amount of a solution containing an $HSO_5^-$ ion, an oxidant, and a metal catalyst or activator for activating the oxidant for a sufficient time and under conditions sufficient to produce a reaction product having less toxicity than the toxic agent. Preferably, the reaction product produced is non-toxic. The non-corrosive compound may include a sorbent gel with the $HSO_5^-$ ion, the oxidant, and the metal catalyst or activator dispersed therein. Preferably, the toxic agent is absorbed into the sorbent gel, which blocks any contact between the toxic agent and the surrounding atmosphere. Once the decontamination reaction has taken place, the compound and reaction product can be easily removed from the surface without damaging the surface. A variety of toxic agents can be decontaminated using this method, including but not limited to mustard gas, G-agents, V-agents, spores and mixtures thereof.

The compound containing $HSO_5^-$ ions is preferably selected from potassium monopersulfate, sodium monopersulfate, ammonium monopersulfate, $HSO_5^-$ salts of other alkali metals, and $HSO_5^-$, salts of alkaline earth metals, most preferably having the formula $2KHSO_5$, $KHSO_4$, $K_2SO_4$. The oxidant can be selected from perborates, persulfates, organic peroxides, alkali metal peroxides, alkali metal superoxides, and alkaline earth metal peroxides, the preferred metal catalyst or activator is ferrous cations.

In yet another embodiment, there is provided a method for preparing a decontamination product. The method includes mixing a compound containing an $HSO_5^-$ ion and an oxidant capable of forming free hydroxyl radicals to form an oxidation component and providing a metal catalyst or activator to bring about the formation of hydroxyl radicals in a separate container. Preferably, the oxidation component is mixed with a sorbent material and the metal catalyst or activator is mixed with a sorbent material. A dispensing element may be provided that mixes the oxidation component with the metal catalyst on demand for easy application of the decontamination product.

BRIEF DESCRIPTION OF THE DRAWINGS

So that the above recited features and advantages of the present invention can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Figure 1:
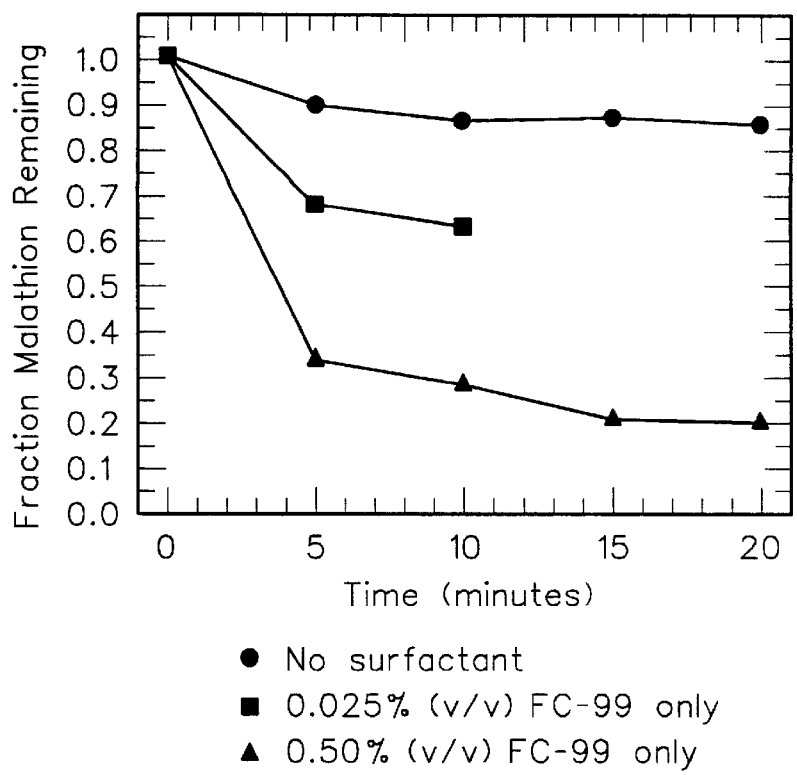
FIG. 1 is a graph showing the destruction of MALATHION under different conditions.

The present invention provides a universal decontamination formulation and method for detoxifying chemical warfare agents (CWA's), biological warfare agents (BWA's) and other toxic agents without producing any toxic by-products, as well as, decontaminating surfaces that have come into contact with these agents.

One aspect of the invention provides a formulation that is universally applicable to decontamination of both biological and chemical agents. The formulation includes a sorbent material or gel, such as fumed silica, a peroxide source such as, hydrogen peroxide ($H_2O_2$), and a peroxide activator, such as iron(II) sulfate, or salts of copper, titanium, chromium, vanadium, zinc, cobalt, and nickel. When the formulation is applied to a biological or chemical agent, the hydrogen peroxide component reacts with ferrous cation to form hydroxyl radicals OH. Hydroxyl radicals react non-selectively and rapidly with most chemical agents, decomposing them to harmless end products. Also included in the formulation is a small amount of a second oxidant $2KHSO_5.KHSO_4.K_2SO_4$, available from the DuPont de Nemoirs Company of Wilmington, Del., under the trademark OXONE. OXONE substantially enhances the formulation's effectiveness against biological agents. The sorbent component is preferably formed of fumed silica (silicon dioxide), a low cost bulk industrial thickening agent used in cosmetics and food preparations. In addition to silicon dioxide, aluminum oxide or titanium oxide may also be used as a delivery agent. Hydrogen peroxide is a widely available low cost bulk commodity which is used at concentrations of 3 wt % as a disinfectant for skin and tissues. The residual gel is self-decontaminating and once dried can easily be wiped from the surface being decontaminated. In addition, the residual gel will have a low environmental impact because it contains only silica and small amounts of colloidal iron oxide (rust).

Another aspect of the invention provides a formulation that has universal chemical and biological decontamination capability. The formulation of the present invention destroys all major classes of CWA's including mustard agents, G-agents and V-agents, such as Tabun (GA), Sarin (GB), Soman (GD), VX, Mustard (HD), as well as bacterial spores, such as Botulinum and viral agents.

In addition to decontaminating chemical and biological agents, the formulation is also effective against other toxic agents such as pesticides. In the experiments shown below, demeton-S, the generic name for O,O-diethyl S-2-(ethylthio)ethyl phosphorothioate, and MALATHION, an organophosphate composition, are used as v-agent surrogates, although both have been used in commercially available pesticides.

The formulation produces sufficient chemical degradation of the CWA's and BWA's to eliminate them and leave no toxic by-products. In addition, the formulation causes little or no damage to the surfaces to which it is applied, making it suitable for use on walls, carpets, and other surfaces that are susceptible to corrosion or etching. The formulation is easily applied by spraying, is highly sorptive and is effective at removing and decontaminating the agents from the surface.

In yet another aspect of the invention, there is provided a method for detoxifying chemical and/or biological warfare agents. The agents are detoxified by reacting the toxic agent with a sufficient amount of a non-corrosive compound containing an $HSO_5^-$ ion, an oxidant, and a metal catalyst or activator for activating the oxidant for a sufficient time and under conditions sufficient to produce a reaction product having less toxicity than the toxic agent. Preferably, the conditions are sufficient that the reaction products are non-toxic and environmentally safe. The underlying surface that the agent is on will also be decontaminated by this method. The reaction can be carried out in an aqueous environment, however, the method preferably includes absorbing the toxic agent into a sorbent gel containing the non-corrosive compound, the oxidant, and the metal catalyst or activator. The gel acts to form a barrier between the toxic agent and the surrounding atmosphere, thereby containing the toxic agent. Once the reaction is complete, the gel containing the compound and the reaction product is removed from the surface without causing any damage to the surface. Thus, the method is effective for detoxifying the toxic agent, as well as decontaminating the exposed surface. The formulation including the gel containing the non-corrosive compound, the oxidant, and the metal catalyst or activator, is effective in decontaminating mustard gas, G-agents, V-agents, and bacterial spores simultaneously.

The compound containing $HSO_5^-$ ions is selected from potassium monopersulfate, sodium monopersulfate, ammonium monopersulfate, $HSO_5^-$ salts of other alkali metals, and $HSO_5^-$ salts of alkaline earth metals or mixtures thereof. Preferably, the compound containing $HSO_5^-$ ions comprises $2KHSO_5$, $KHSO_4$, $K_2SO_4$ and is sold under the commercial name OXONE. OXONE has a powerful oxidation potential and has seen limited use as a decontamination agent. It has been shown that OXONE is effective against HD and VX type agents. However, OXONE appears to be ineffective against G-agents. $KHSO_5$, the active ingredient in OXONE, is prepared by a variety of methods involving either $H_2O_2$ and chlorosulfonic acid or potassium persulfate and $H_2SO_4$.

The chemical formula of the compound is shown below.

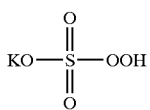

The oxidant may be selected from perborates, persulfates, organic peroxides, alkali metal oxides, alkali metal peroxides or mixtures thereof. Preferably, the oxidant is hydrogen peroxide. Preferably, the hydrogen peroxide is catalyzed or activated by a metal, selected from iron and iron salts, preferably, the metal activator is $Fe^{2+}$ in the form of Fenton's reagent. The oxidation of the toxic agents and their by-products is primarily based on $Fe^{2+}$ activated hydrogen peroxide.

The activated hydrogen peroxide reaction is given in Eq. 1.

$$Fe^{2+}+H_2O_2 \rightarrow Fe^{3+}+OH.+HO^- \qquad (1)$$

yielding hydroxyl radicals (OH.), one of the most powerful oxidants.

The decomposition of $H_2O_2$ is extremely sensitive to catalysis or activation (both heterogeneous and homogeneous) by a wide variety of substances.

$$H_2O_2 \rightarrow H_2O+O_2 \qquad (2)$$

Both $Fe^{2+}$ and $Fe^{3+}$ react with hydrogen peroxide. The "classical" mechanisms for these reactions involve hydroxyl radical intermediates that can attack organic compounds. The classical reaction of $Fe^{2+}$ with $H_2O_2$, known as the Fenton reaction, generates HO. in the rate-limiting step (Eq. 3). Reaction with another $Fe^{2+}$ (Eq. 4) or reaction with an organic compound may scavenge HO.

Typical rates of reaction between hydroxyl radicals and organic materials are $10^9$–$10^{10}$ ($M^{-1} s^{-1}$).

$$Fe^{2+}+H_2O_2 \rightarrow Fe^{3+}+OH.+OH^- \qquad (3)$$

$$OH.+Fe^{2+} \rightarrow Fe^{3+}+OH^- \qquad (4)$$

$Fe^{3+}$ decomposes $H_2O_2$ to $O_2$ and $H_2O$. The classical "radical chain" mechanism proposed for simple $Fe^{3+}$(aq) systems (i.e., no complexing ligands other than water) involves HO. and the hydroperoxyl radical ($HO_2$.) by the following steps, inclusive of Equations (3) and (4):

$$Fe^{3+}+H_2O_2 \rightarrow Fe-OOH^{2+}+H^+ \qquad (5)$$

$$Fe-OOH^{2+} \rightarrow HO_2.+Fe^{2+} \qquad (6)$$

$$Fe^{2+}+HO_2. \rightarrow Fe^{3+}+HO_2^- \qquad (7)$$

$$Fe^{3+}+HO_2. \rightarrow Fe^{2+}+O_2+H^+ \qquad (8)$$

$$HO.+H_2O_2 \rightarrow H_2O+HO_2. \qquad (9)$$

In the presence of excess peroxide, the concentration of $Fe^{2+}$ is small relative to the concentration of $Fe^{3+}$, since reaction (6) is generally much slower than reaction (3). Reaction (9) is an additional mechanism for HO. scavenging.

Compared to HO., $HO_2$. is much less reactive, and its conjugate base $O_2.^-$ ($pK_a$, 4.8) is practically unreactive as a free radical. Carbon-centered radicals generated by hydroxyl radical attack may react with $O_2$, if present, to give organoperoxy radicals (ROO.), which can decompose to form $HO_2$. or ultimately nonradical oxygenated products.

In addition to iron, it is preferred that the formulation include phosphate ions. The phosphate ions act as a masking agent that slows the release of the $Fe^{2+}$ available for the generation of OH. radicals from $H_2O_2$.

The ideal gel or delivery agent for the decontamination formulation is one that is inert or non-reactive with the oxidizing agents. Fumed silicon dioxide ($SiO_2$) has shown goods results. Fumed silica has an extremely small particle size (0.007 to 0.014 μm), enormous surface area (about 200 $m^2/g$), high purity (99.8%), and a low bulk density (250 $kg/m^3$). Fumed silica performs the two primary functions of reinforcement and rheology (flow) control in the present delivery system. Reinforcement increases the strength or viscosity of various materials, such as the decontaminating agents, allowing them to be used in a wider number of applications, such as on ceilings and walls. The viscosity of the gel can be easily tailored to suit a specific situation. Fumed silica is prepared by gas/oxygen flame oxidation of $SiCl_4$ or methyltrimethoxysilane as shown in Scherer, G. W. and Bachman, D. L. "Sintering of Low-Density Glasses: II, Experimental Study." J. Amer. Ceramic Soc. 60, 239 (1977).

Fumed silica is widely available and is generally used in small quantities in many products such as toothpaste, detergents, food, coatings, adhesives, concrete, cosmetics, inks, plastics, and various types of rubbers. Fumed silica acts to thicken, and suspend solids. Fumed silica gel provides good surface coverage because of its free flowing character and holds the reactive components of the formulation in-place for extended periods. Sorption of the contaminant into the gel matrix is highly effective because of the enormous surface area the fumed silica provides and because of the relatively large volume available for dissolution.

Six chemical surrogates (1 mustard, 3 G-agents, and 2 V-agents) were selected along with *Bacillus subtilus* globigii spores, which is the standard surrogate for Bacillus anthracis (anthrax) spores, for experiments with the decontamination system of the present invention. The structure of the six chemical surrogates used in these experiments are shown below. Initially, only one V-agent surrogate (MAL) was selected for testing; however, an additional V-agent surrogate, Dem-S which more closely resembles VX at the phosphorous was selected for testing.

Mustard surrogate
(CEES)

V-Agent surrogate
(Dem-S)

-continued

V-Agent surrogate
(MAL)

G-Agent surrogate
(DMMP)

G-Agent surrogate
(DEMP)

G-Agent surrogate
(DIMP)

The following examples serve to illustrate the invention and are therefore not to be considered limiting of its scope.

MATERIALS USED IN EXAMPLES

Unless otherwise indicated, the following materials and reagents were used in the examples described below.

Surrogates: Dimethylmethylphosphonate (DMMP) and Chloroethylethyl-sulfide (CEES)- Aldrich Chemical Co., 1001 West Saint Paul Ave., Milwaukee, Wis. 53233; Diethylmethylphosphonate (DEMP); Diisopropylmethylphosphonate (DIMP)—Alfa Aesar, 30 Bond St., Ward Hill, Mass. 01835; MALATHION (MAL)—Pfaltz & Bauer, 172 E. Aurora St., Waterbury, Conn. 06708; Demeton-S (Dem-S)—ChemService, 660 Tower Lane, West Chester, Pa. 19381; and *Bacillus subtilus* (globigii) spores—STERIS Corp., 5960 Heisley Road, Mentor, Ohio 44060.

Reagents: Hydrogen Peroxide (3 wt %)—Walmart, College Station, Tex. 77840; Phosphoric Acid (85 wt %), and Dichloromethane (Suitable for GCDMS)—Fisher Scientific, 711 Forbes Avenue, Pittsburgh, Pa. 15219; Sodium Hypochlorite (13 wt %), OXONE, Hydrogen Peroxide (30 wt %), Ferrous Sulfate Heptahydrate, Sodium Hydroxide, Chloroethylphenyl Sulfide (CEPS) were all purchased from Aldrich Chemical Co.

Example 1

CEES Oxidation at 50:1

1.5mL of freshly prepared gel containing 8 wt % fumed silica suspended in a 0.1 M sodium phosphate buffer, pH=3.2, was added to a 20 mL vial containing 0.13 grams $FeSO_4.7H_2O$ (0.45 mmol). The vial was shaken/swirled until all the iron had gone into solution. 12 μL CEES (0.1 mmol) was then added to the vial and the vial was shaken/swirled. 0.51 mL $H_2O_2$ (30 wt %, 4.5 mmol) and 77 mg OXONE (0.5 mmol) was added, the vial was capped with a TEFLON lined cap and shaken to mix reagents. The vial was allowed to stand throughout the reaction.

At the desired time, the reaction was quenched by the addition of 20 mL dichloromethane followed by vigorous shaking for 2–3 minutes. 10 μL CEPS (as the internal standard) was added and the vial was shaken for another 3–4 minutes. The capped vial was allowed to stand for 30 minutes and a 2 mL sample was withdrawn from the lower, organic phase and placed in a 2 mL autosampler vial.

Example 2

CEES Oxidation at 20:1

1.5 mL of freshly prepared gel containing 8 wt % fumed silica suspended in a 0.1 M sodium phosphate buffer, pH=3.2, was added to a 20 mL vial containing 56 mg $FeSO_4.7H_2O$ (0.2 mmol). The vial was shaken/swirled until all the iron had gone into solution. 12 μL CEES (0.1 mmol) was then added to the vial and the vial was shaken/swirled. 0.57 mL $H_2O_2$ (12 wt %, 2 mmol) and 31 mg OXONE was added, the vial was capped with a TEFLON lined cap and shaken to mix reagents. The rest of the method was identical to that mentioned above in Example 1.

CEES Detection and Quantitation

A Varian Saturn 4D GC/MS/MS System was used to detect and quantitate CEES and CEPS (internal standard). The Saturn 4D system is composed of: (1) Model 8200 Autosampler; Star 3600 CX GC with a Model 1094 Septum-equipped Programmable Injector (SPI); (2) 30 meter×0.25 id×0.25 μm stationary phase DB-5MS capillary column or equivalent; (3) Saturn 4D MS/MS Ion Trap Mass Detector; and (4) a Digital PC Computer equipped with NIST MS database software for control, identification and data processing. All samples were injected in triplicate to minimize variations from individual runs. The GC conditions were: injector temperature: 270° C.; segment 1: 80–180° C. at 8° C./min; segment 2: 180° C. and hold for 3 min; transfer line: 180° C.; manifold temperature: 250° C. The MS settings were: mass range: 50–180 m/z(mass to charge ratio); scan time: 1.000 seconds; segment length: 15 minutes; Fil/Mult (Filament Multiplier) delay: 2.6 minutes; peak threshold: 1 count; background mass: 10 m/z. The carrier gas was ultra-high purity Helium, greater than 99.999% purity with a linear velocity of 25 cm/min. An additional oxygen trap was added to the line to protect the column and ion trap. The sample injection volume for all samples was 0.3 μL.

Example 3

DMMP, DEMP, and DIMP Oxidation at 100:1

1.5 mL of freshly prepared gel containing 12 wt % fumed silica suspended in a 0.1 M sodium phosphate buffer, pH=3.2, was added to each of three 40 mL vials containing 12 μL DMMP, 15 μL DEMP and 18 μL DIMP, respectively. A 0.5 mL water solution containing 0.28 g $FeSO_4.7H_2O$ was added to the vials. The vials were shaken/swirled to mix reagents. 1.03 mL $H_2O_2$ (30 wt %) and 0.154 g OXONE were added to each vial, the vials were capped with a TEFLON lined cap and shaken to mix reagents. Each vial was allowed to stand throughout the reaction. By allowing each vial to stand, removal of the surrogate from glass was simulated At various time intervals of interest, the reaction was quenched by the addition of 20 mL dichloromethane followed by vigorous shaking for 2–3 minutes. 10 μL DMMP (as the internal standard) was added and the vial was shaken for another 3–4 minutes. (When the destruction of DMMP was being measured, DEMP was used as the internal standard). The capped vial was allowed to stand for 30 minutes and a 2 mL sample was withdrawn from the lower, organic phase and placed in a 2 mL autosampler vial.

DMMP, DEMP, and DIMP Detection and Quantitation

The same GC/MS system used to detect and quantify CEES was used for the detection and quantitation of DMMP, DEMP, and DIMP. The GC conditions were: injector temperature: 270° C.; segment 1: 50–200° C. @ 8° C./min; segment 2: 200° C. and hold for 2 min; transfer line: 180° C.; manifold temperature: 250° C. The MS settings were: mass range: 40–175 m/z; scan time: 0.500 seconds; segment length: 8 minutes; Fil/Mult. delay: 4.0 minutes; peak threshold: 1 count; background mass: 10 m/z.

Example 4

Dem-S at 100:1 and MAL Oxidation at 1000:1

2 mL of freshly prepared gel containing 6 wt % fumed silica and 12.6 mg/mL $FeSO_4.7H_2O$ was added to a 20 mL vial containing 24 μL Dem-S and a vial containing 2.5 μL MAL. 15 mg of OXONE and 100 μl of 30 wt % $H_2O_2$ were simultaneously added to each vial and vortexed. At the desired time, the reaction was quenched by the addition of 18 mL of quenching solution which consisted of 10% isopropanol, 27% acetonitrile, and 63% water (actually 10% isopropanol and 90% liquid chromatograph mobile phase).

Dem-S and MAL Detection and Quantitation

The quantitation of Dem-S and MAL was accomplished primarily by liquid chromatography (LC). The LC system was composed of two Shimadzu LC-6 reciprocating piston pumps, a Rheodyne 6-port manual injector fitted with a 100 μl injection loop, an Econosphere 3 μm, 4.6×25 mm C18 column, and a variable wavelength Shimadzu 6AV UV/VIS detector. The whole system was controlled by EZChrom software running on an IBM compatible PC with an Intel 486SX processor. The mobile phase for both Dem-S and MAL was 30% acetonitrile/70% water at 2.0 mL/min. The wavelength monitored was 210 nm. All gel samples were routinely passed through a 0.45 μm filter to remove the gel prior to performing LC.

Example 5

*Bacillus subtilus* Spore Oxidation

100 μL of $1.3 \times 10^9$ spores/mL ($1.3 \times 10^8$ spores) were heat fixed onto autoclaved glass slides. After exposure to the decontaminant gel, the slides were washed with 30% ethanol to quench the reaction and were placed into a test tube containing 3 mL of 20 mM potassium phosphate buffer, pH 7.1. A control was also tested by treating slides with the 0.1 M phosphate pH 3.2 buffer. The control was exposed for the duration of the experiment and was similarly washed with 30% ethanol and placed into a test tube containing 3 mL of 20 mM potassium phosphate buffer, pH 7.1.

*Bacillus subtilus* Spore Detection and Quantitation

After collecting slides at all time points, the test tubes containing the slides were sonicated for one hour to extract the spores off of the slides. The buffer containing the extracted spores was then serially diluted to $10^{-6}$ and 100 µL duplicates were plated onto nutrient agar out to a dilution factor of $10^{-7}$. The plates were incubated for 24 hours and colony forming units were counted. This method has a 99.8% spore recovery rate. The maximum number of spores plated equals the number of spores on the slide ($1.3 \times 10^8$) divided by the spore recovery volume (3 mL) times the volume plated (0.1 mL) which equals $4.3 \times 10^6$. The detection limit is one spore per plate out of $4.3 \times 10^6$ which corresponds to a 6.6 log (log $4.3 \times 10^6$—log 1) or 99.99998% detection limit.

Example 6

Spiking and Decontamination of Carpet Swatches

A sample of commercially available carpet was cut into squares having sides 2½ inches long. Two squares were used for the experiment. Each of the two squares was spiked with 27 µl of Dem-S (about 30 mg, 0.12 mmole). The 27 µl was distributed as nine 3 µl spots arranged in a 3×3 matrix on the square. Each swatch was placed in a glass beaker. To the control swatch 25 mL quenching solution (10% isopropanol/ 90% LC mobile phase) was added and to the other swatch 25 mL of freshly prepared decontamination gel was added. The gel concentration was 3.1 wt % $H_2O_2$, 2.5 wt % $FeSO_4.7H_2O$, 1.5 wt % OXONE, and 6 wt % fumed silica. This corresponded to a 200:1 molar excess of oxidant to surrogate. After 5 minutes had elapsed, 25 mL of quenching solution was added to each swatch for a total volume of 50 mL in each. 3 mL of each was filtered and injected into the LC system previously described. Both swatches were removed from the beakers and the treated swatch was washed with 25 mL of water to remove the gel.

Example 7

Material Compatibility Testing

In addition to the carpet decontamination mentioned above, other materials were treated with the gel, prepared according to Example 10, to determine material compatibility. A single 150 g piece of concrete was placed in a beaker and submerged in decontaminating gel. After an hour of exposure, the concrete was removed, rinsed with water and visually examined for damage compared to an adjacent untreated sample.

Example 8

Similarly, a 1 inch×2 inch coupon of aluminum was submerged for an hour in decontaminating gel prepared according to Example 10. After being rinsed with water, the coupon was closely examined next to an untreated aluminum coupon.

Example 9

Painted dry-wall coupons were also exposed to gel prepared according to Example 10. First the coupons were prepared by applying three coats of red indoor latex enamel paint to a large sheet of ⅜ inch dry-wall. Both paint and dry-wall were purchased at a local home improvement store. A section of the sheet was cut into square coupons having 2½ inch sides. To the painted surface of a single piece of painted dry-wall was placed 1 mL of decontaminating gel. This limited volume was selected to expose only the paint on the coupon to the gel and not the unpainted sides of the coupon. The gel was allowed to dry overnight (about 16 hrs). The next day, the dried gel was wiped clean from the painted surface with a damp cloth. The painted surface was visually inspected for noticeable damage adjacent to a similar coupon that was untreated. Similarly, a carpet swatch, identical to those mentioned above, was treated with 1 mL of gel overnight. The next day the swatch was rinsed and compared to a similar untreated swatch.

Example 10

Spray Testing

The decontamination formulation was prepared by mixing 2.71 L of 0.1 M sodium phosphate buffer pH 3.2, 0.14 L deionized water, 121.6 g of $FeSO_4.7H_2O$ and approximately 450 g of flumed silica in a 10 quart container. The silica was added last with the aid of an impeller until the mixture was as thick as possible before adding the following reagents. In a separate container, 73.15 g of OXONE, 0.5 L of 30 wt % $H_2O_2$ and approximately 100 g of silica were mixed together until the gel was a thick consistency. The two gels were then mixed together to give a final gel concentration of about 14% by weight.

Results

The experiments performed in Examples 1-4 compared activated peroxide to OXONE for the oxidation of surrogates. OXONE rapidly oxidized CEES and Dem-S to completion in 5 minutes, but could only eliminate 11% of DEMP after 30 min at a 100:1 molar excess of OXONE to surrogate. Catalyzed peroxide (also at 100:1) produced similar rapid destruction of CEES and Dem-S and also eliminated 77% of DEMP in 5 minutes. More importantly, when the oxidants were combined in a 90:10 ratio of catalyzed or activated peroxide:OXONE, the resulting formulation eliminated 98.8% of DEMP in 5 minutes while maintaining its effectiveness against CEES and Dem-S (Table 1).

In addition to the synergy observed in the destruction of chemical agents, the 90:10 combination of peroxide to OXONE also proved substantially more effective against spores than either of the oxidants alone (See Example 11 below).

1. Chemical Decontamination

The ability of the 90:10 peroxide to OXONE, formulation to destroy all six chemical surrogates in the gel is described below. The results are summarized in Table 1. Below each of the surrogates is listed the initial concentration of peroxide, OXONE, iron, and surrogate in the reaction, followed by the percent of initial surrogate remaining in the reaction at different time points.

It is important to note that both the concentrations of oxidant and surrogates in the reactions listed in Table 1 are environmentally safe. A 0.9 M solution of peroxide is equivalent to about 3 wt % which is equivalent to peroxide solutions available at local supermarkets and used as a topical disinfectant and mouthwash. The highest concentration of peroxide in the table is 2.3 M or about 8 wt %/, The initial concentration of surrogates used in the reactions listed in the table range from 1 to 50 mM which is in the range of the concentrations typically encountered under field decontamination situations ($10^{-2}$–$10^{-1}$M).

All of the reactions were performed in a mixture whose total peroxide concentration equaled 0.9 M. CEES (at a total oxidant to CEES ratio of 20:1), Dem-S and MAL where all decontaminated at this concentration. In the CEES (50:1), however, the GC/MS detection limit for CEES prevented using 20 mM surrogate with the 0.9 M peroxide/0.1 M OXONE decontamination gel. A higher concentration of CEES was required and to preserve the molar ratio of oxidant to surrogate, a more concentrated gel formulation was used. Similarly, the GC/MS detection limit prevented using a 10 mM initial concentration for the G-agent surrogate experiments and higher concentrations of both surrogate and oxidants were necessary to preserve the 100:1 molar ratio of oxidant to surrogate.

From the data presented in Table 1, it is obvious that the gel is a very effective decontaminant because of the six surrogates listed in the table, detectable amounts of CEES and Dem-S are not present at 3 minutes and detectable amounts of DEMP and DIMP are not present after 10 minutes. DMMP is reduced to less than 1% in 30 minutes and MAL, a typically very difficult surrogate to oxidize, is reduced to about 6% of its original concentration in 90 minutes.

Inspection of Table 1 reveals that DMMP is a more persistent surrogate than either DEMP or DIMP, although the reason for this observation is currently unknown. In the literature, there are examples of the decontamination of GB and GD in OXONE solutions. It was reported that neither oxidation nor displacement of the OR groups is observed in solutions containing 50 mM agent and 100 mM OXONE at pH 2. Yang, Y. C., Baker J. A. & Ward, J. R., Chem. Rev. 1992 Vol. 91 p. 1729–1743. In fact, simple hydrolysis of the P-F bond to form the corresponding phosphonic acids is the exclusive hydrolysis pathway and results in greater than 90% destruction of GB in 2 hours and greater than 90% destruction of GD in 5 hours. In the reactions described in Table 1, the initial surrogate concentration is 25 mM; the initial OXONE concentration is 250 mM; and the pH is about 2. Of course, peroxide and iron catalyst or activator are also present resulting in a large excess of oxidant to surrogate and greater than 90% destruction of all surrogates occurs in less than 5 minutes. With the large excess of oxidant present in the reactions listed in Table 1, it is possible that oxidation of the G-agent surrogates is occurring.

The most likely mechanism of destruction of the G-agent surrogates in the reactions in Table 1 is by hydrolysis, particularly when considering that DMMP is the most persistent of the three surrogates. Hydrolysis of the surrogates involves an $SN^2$ attack on the phosphorous atom resulting in inversion about the phosphorous and release of the OR group generating the corresponding phosphonic acid. When comparing the three G-agent surrogates and the chemistry of an $S_N2$ attack on each, it is apparent that DMMP should be the most persistent since it has the least stable leaving group, -Omethyl. Conversely, DIMP should be the easiest of the three to destroy because it has the best leaving group, -Oisopropyl. The data in Table 1 certainly agrees with this trend.

Dem-S, which more closely resembles VX at the phosphorous group, was no longer detected at 3 min. In addition to the sulfur directly bound to the phosphorous, Dem-S has a highly accessible sulfur atom in the long hydrophobic chain and it is this sulfur that is the most likely the first atom

TABLE 1

Representative chemical surrogates from the three main classes of chemical warfare agents are destroyed with the gel formulation in less than 90 minutes. Numbers in the table express the percent of surrogate remaining at the times listed.

| | Mustard Surrogate | | | G-Agent Surrogates | | V-Agent Surrogates | |
|---|---|---|---|---|---|---|---|
| | CEES | CEES | DMMP | DEMP | DIMP | Dem-S | MAL |
| | 0.9 M $H_2O_2$ | 1.8 M $H_2O_2$ | 2.3 M $H_2O_2$ | 2.3 M $H_2O_2$ | 2.3 M $H_2O_2$ | 0.9 M $H_2O_2$ | 0.9 M $H_2O_2$ |
| | 0.1 M OXONE | 0.2 M OXONE | 0.25 M OXONE | 0.25 M OXONE | 0.25 M OXONE | 0.1 M OXONE | 0.1 M OXONE |
| | 0.1 M $Fe^{2+}$ | 0.18 M $Fe^{2+}$ | 0.25 M $Fe^{2+}$ | 0.25 M $Fe^{2+}$ | 0.25 M $Fe^{2+}$ | 0.09 M $Fe^{2+}$ | 0.09 M $Fe^{2+}$ |
| | 6 wt % silica gel | 6 wt % silica gel | 6 wt % silica gel | 6 wt % silica gel | 6 wt % silica gel | 6 wt % silica gel | 6 wt % silica gel |
| Time (min) | 50 mM CEES (20:1) | 40 mM CEES (50:1) | 25 mM DMMP (100:1) | 25 mM DEMP (100:1) | 25 mM DIMP (100:1) | 10 mM Dem-S (100:1) | 1 mM MAL (1000:1) |
| 0 | 100% | 100% | 100% | 100% | 100% | 100% | 100% |
| 3 | 71% | ND | — | — | — | ND | — |
| 5 | 59% | ND | 4.7% | 1.2% | 0.2% | — | 18% |
| 10 | — | — | — | ND | ND | ND | — |
| 15 | — | ND | 5.7% | ND | ND | — | 13% |
| 20 | — | — | — | — | — | ND | — |
| 30 | 0.6% | ND | 0.9% | ND | ND | — | — |
| 60 | — | — | — | — | — | ND | — |
| 90 | ND | — | — | ND | ND | ND | 6.3% |

ND — None detected (less than 0.1%)

to be oxidized in the molecule followed by the sulfur proximal to the phosphorous.

Conversely, MAL persisted after 90 minutes when exposed to a 1,000 fold molar excess of oxidant. While collecting data for MAL presented in the above table, small droplets were observed in the gel suggesting that the poor solubility of MAL in the aqueous decontaminating solution could be the reason for the slow kinetics of oxidation observed. Therefore, an additional MAL oxidation experiment was performed to examine the ability of a fluorinated surfactant (FC-99, 3M Specialty Chemicals Division) to enhance the solubility and therefore, oxidation of MAL. The gel was omitted from this experiment in order to carefully observe whether MAL was completely solubilized in the test samples. In addition, the concentration of MAL was increased by a factor of 20 (20 mM) when compared to the reaction described in Table 1. This decreased the molar excess of oxidant from 1,000:1 to 50:1.

In the absence of surfactant, MAL droplets were observed in solution and as shown in FIG. 1, 85% of MAL was still present after 20 minutes. This data is certainly comparable to that presented in Table 1. However, in the sample that contained 0.025% FC-99, MAL droplets were still visible in the decontaminating solution but a noticeable enhancement of MAL destruction was observed. When FC-99 was increased to 0.50% in the decontaminating solution, MAL droplets were not observed in solution and 80% of the MAL was destroyed in 20 minutes, certainly a substantial enhancement considering 20 times more MAL was oxidized with the same amount of oxidant. This data suggests that the solubility of MAL in aqueous solution may be a barrier to oxidation and that by increasing MAL solubility, decontamination levels comparable to other surrogates can be achieved. A small amount of non-oxidizable surfactant and/or cosolvent (i.e. acetonitrile) could be used as additional ingredients in the decontamination solution to enhance destruction of very hydrophobic agents including thickened agents.

2. Biological Decontamination

The data represented in Table 1 and FIG. 1 show that the decontamination gel can destroy six widely acceptable chemical surrogates at battlefield relevant concentrations. However, a universal decontaminant must also be able to destroy biological warfare agents. Many biological warfare agents, such as Staphylococcal enterotoxin and substance P, are proteinaceous and highly susceptible to chemical oxidation. Small changes in the molecule can dramatically destabilize the overall three dimensional structure, rendering the agents harmless. A substantial challenge in biological warfare agent decontamination are bacterial endospores.

Example 11

Figure 2:
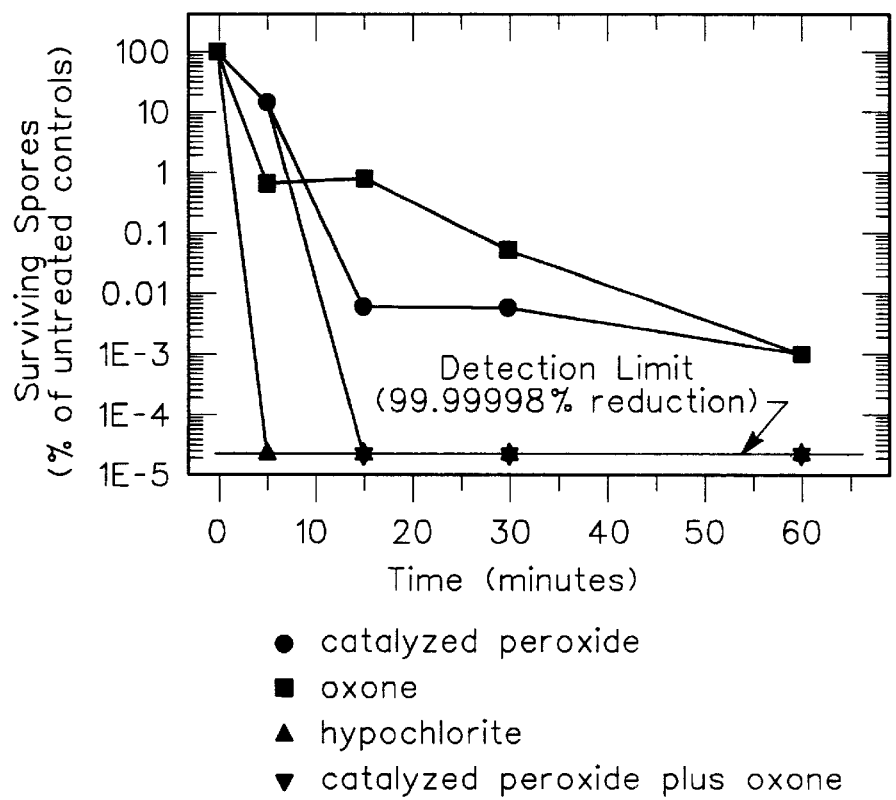
FIG. 2 is a graph showing the destruction of spores using various oxidant formulations.

*Bacillus subtilus* globigii spores, a surrogate for Bacillus anthracis (anthrax). $1.3 \times 10^8$ spores were heat fixed onto a glass slide and the slide was submerged into 8 mLs of either (a) 1.3 M catalyzed or activated peroxide, (b) 0.13 M OXONE; (c) 0.13 M hypochlorite; or (d) a combination of 1.3 M catalyzed or activated peroxide and 0.13 M OXONE. The results of this experiment are presented in FIG. 2 with the detection limit representing. 10 spores/mL or a 99.99998% reduction in surviving spores (a 6.6 log reduction). The figure shows that hypochlorite is the most effective, eliminating all detectable spores within the first 5 minutes. The decontamination solution was almost as effective, eliminating all detectable spores by the next time point (15 minutes).

It is significant that catalyzed or activated peroxide and OXONE together gave substantially faster spore deactivation than either of them used individually. It is believed that the peroxide, at a relatively high concentration, is able to penetrate the spore coat increasing its permeability to OXONE. In this way, OXONE can then exert a more potent biocidal effect on the spore than if it were used on its own. Regardless of the mechanism of spore deactivation, the results shown in FIG. 2 clearly demonstrate that a catalyzed or activated peroxide-OXONE formulation is suitable as a decontaminant for biological as well as chemical agents. Data shown later confirm that the spore deactivation rates can be achieved in the gel formulation as well as in the liquid medium used in FIG. 2.

Example 12

Elimination of by-Products: Liquid Formulation Studies

An experiment was performed to determine if the standard oxidation formulation produced chloroethyl ethyl sulfoxide, chloroethyl ethyl sulfone, or any other by-product during CEES oxidation and more importantly if these by-products persisted. Initially, this experiment was performed in the liquid state and the ratio of oxidant to CEES was 10:1. The reaction mixture was extracted into dichloromethane and injected into the GC/MS system for peak quantitation and identification. The experiment compared catalyzed or activated peroxide to OXONE and a combination of the two oxidants. Data was collected at 3 minutes and 90 minutes the peak areas of CEES and the four by-products are shown in FIG. 3 (3 minutes) and FIG. 4 (90 minutes).

Figure 3:
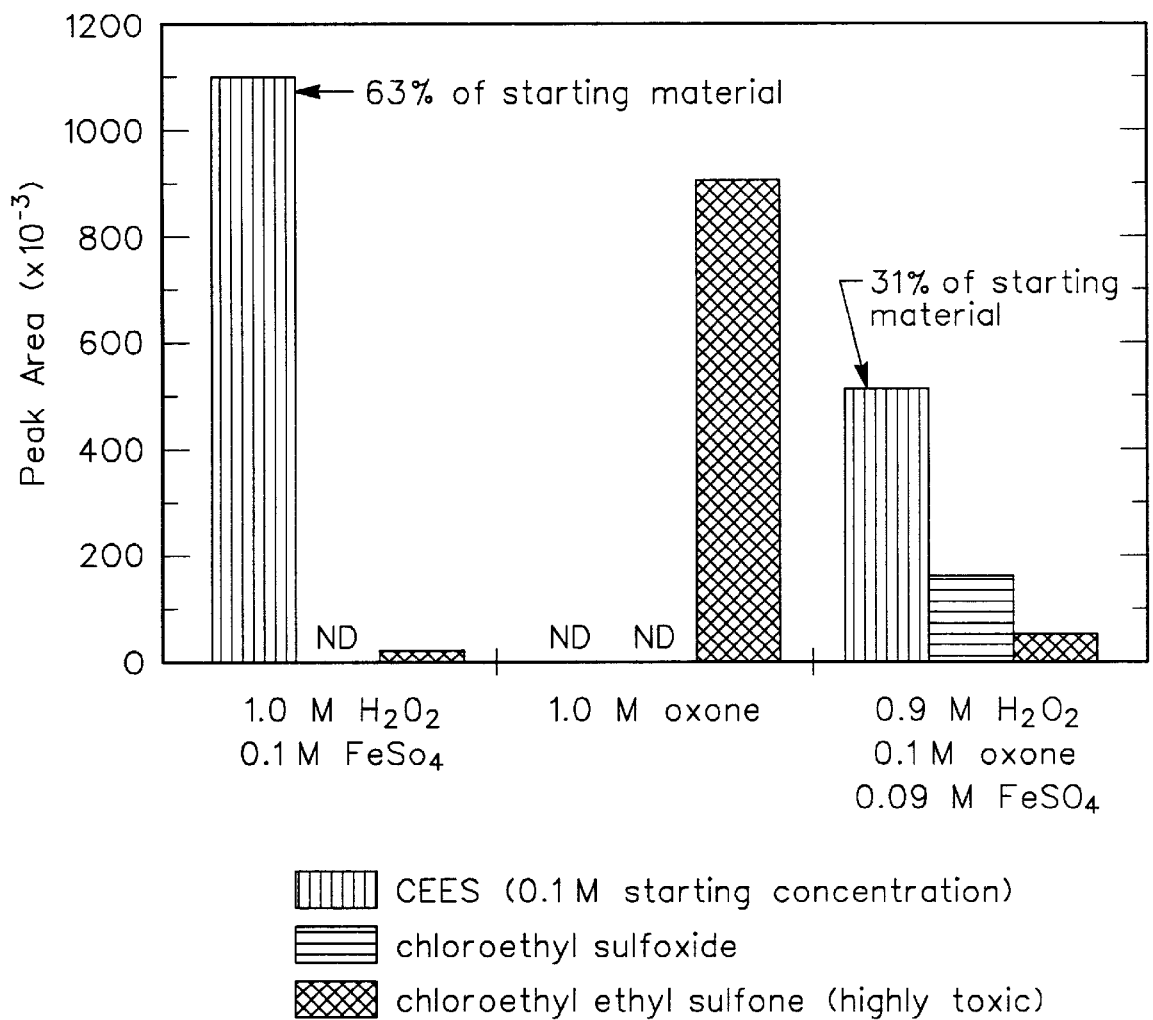
FIG. 3 is a bar graph showing the presence of intermediates after treatment with a formulation of the present invention.

The three decontaminating formulations presented in FIG. 3, did not generate any of the dechlorinated intermediates, in the hypochlorite oxidation of CEES. The results from this experiment demonstrate that a combination of catalyzed or activated peroxide and OXONE is better than either oxidant alone. As shown in FIG. 3, 37% of the CEES is destroyed by catalyzed or activated peroxide, 100% by OXONE and 69% by the 90:10 catalyzed or activated peroxide:OXONE combination. In this regard, OXONE is clearly superior. However, no by-products, are detected in the catalyzed or activated peroxide oxidation of CEES while a substantial amount of chloroethyl ethyl sulfone is detected in the OXONE oxidation of CEES. It is important to remember that the corresponding intermediate in the oxidation of mustard is bis(2-chloroethyl)sulfone which is reported to be the most toxic of the S-oxidation products. By-products in the catalyzed or activated peroxide:OXONE combination are detected but in very small amounts.

Figure 4:
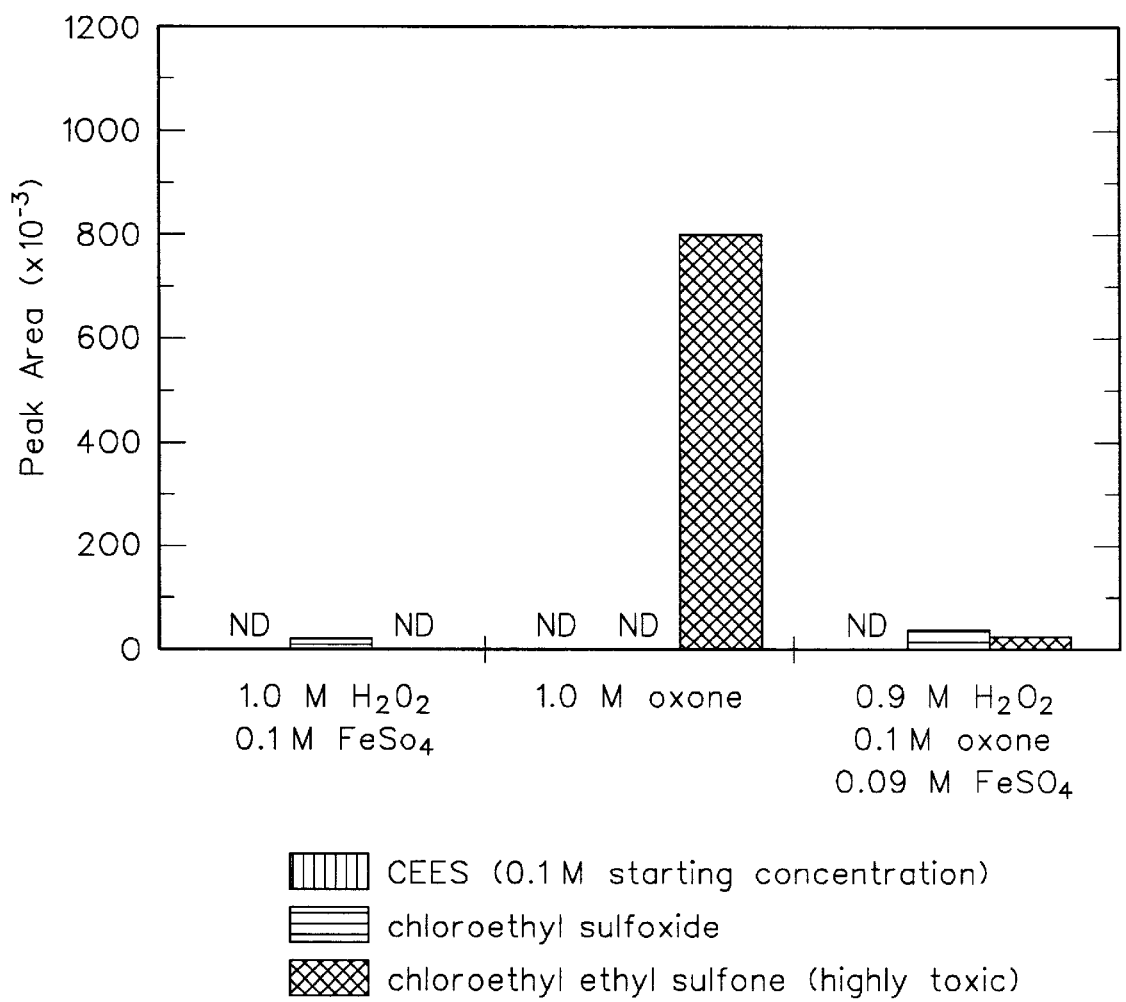
FIG. 4 is a bar graph showing the elimination of intermediates after treatment with a formulation of the present invention.

As shown in FIG. 4, by 90 minutes both catalyzed or activated peroxide alone and the catalyzed or activated peroxide:OXONE combination have completely eliminated CEES. The toxic sulfone detected in the OXONE oxidation of CEES at 3 minutes is still present. The small amounts of the sulfoxide and the sulfone present at three minutes (FIG.

3) in the catalyzed or activated peroxide, OXONE mixture have decreased by 90 minutes. These experiments provide a good example of why the mixed oxidant formulation is used for the decontamination gel. The mixed oxidant (catalyzed or activated peroxide plus OXONE) provides both rapid degradation of CEES while considerably reducing and practically eliminating by-products. The four main by-products identified in the oxidation of CEES have the following structures:

ethylethylenesulfoxide ethylethylenesulfone chloroethylethylsulfoxide chloroethylethylsulfone Chloroethylethylsulfone is particularly undesirable since the corresponding intermediate in the oxidation of mustard (bis(2-chloroethyl)sulfone) is extremely toxic.

Example 13

Elimination of by-Products: Gel Formulation Studies

Figure 5:
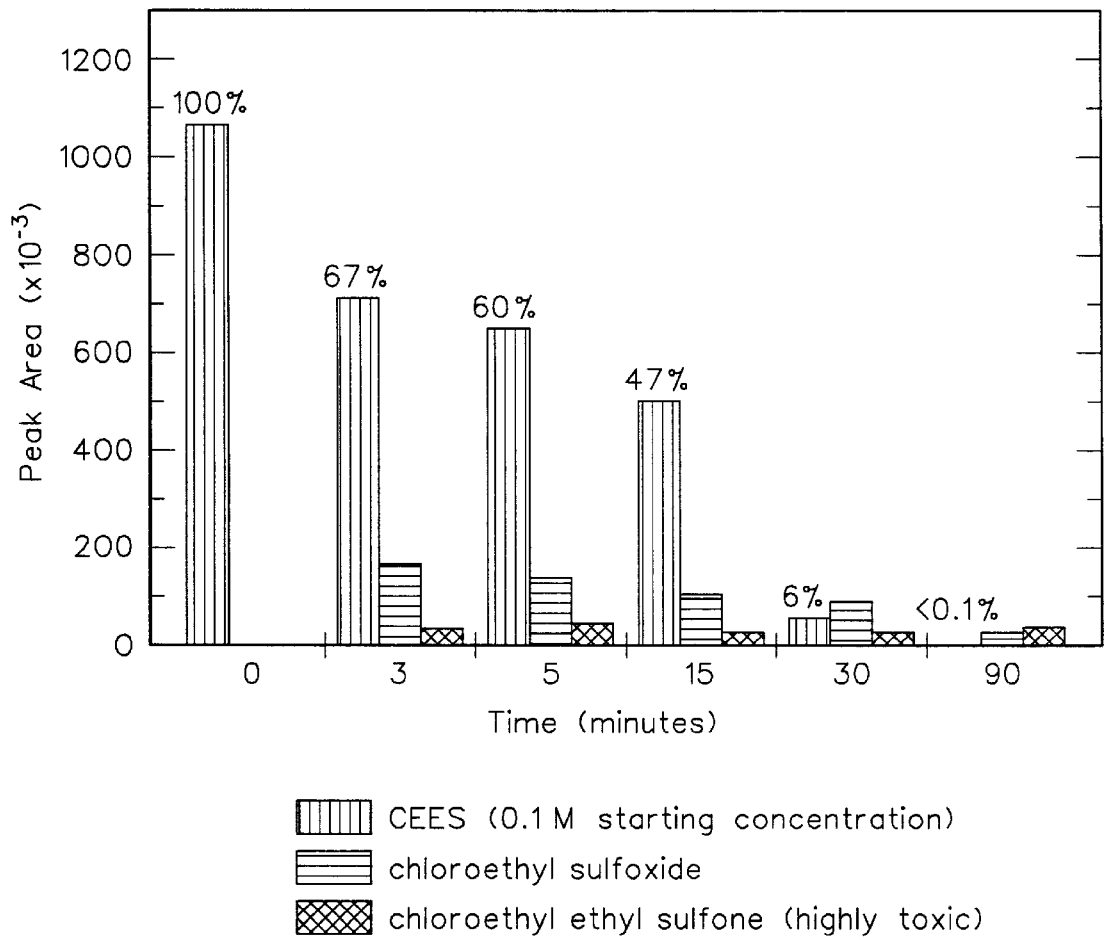
FIG. 5 is a bar graph showing the concentrations of the Mustard surrogate, chloroethyl ethyl sulfoxide, and chloroethyl ethyl sulphone over time after treatment with a formulation of the present invention.

In this experiment, the mixed oxidant experiment in Example 12 was repeated using the gel. Additional time points were collected to more closely monitor the formation and subsequent disappearance of the by-products with time. The results from this experiment appear in FIG. 5. The bars in the figure represent the concentration of CEES with time as determined by peak areas in the GC chromatogram. When the liquid and gel oxidation of CEES are compared, it is apparent that the destruction of CEES occurs more slowly in the gel. At three minutes in the liquid formulation, only 31% of the original CEES remained (See FIG. 3), while 67% of the original CEES remained in the gel formulation. Nevertheless, at ninety minutes, in either formulation, no CEES was detected and only small quantities of by-products were observed.

As expected, this experiment suggests that the decontamination rate is inversely proportional to the viscosity of the gel, possibly implicating diffusion as a rate limiting factor in decontamination. Therefore, the decontamination data collected in the gel from Table 1 could be even faster if the amount of fumed silica was decreased in the formulation.

Example 14

Figure 6:
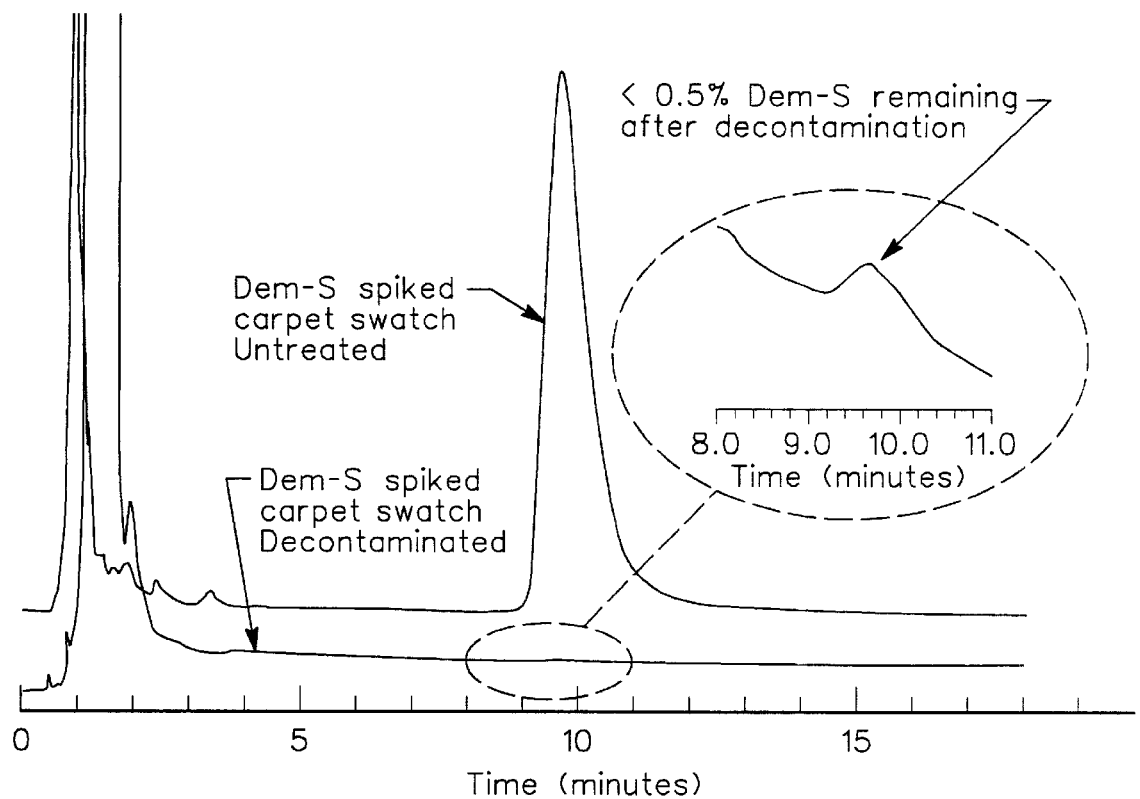
FIG. 6 is a liquid chromatogram of the remaining V-agent surrogate concentration in a carpet swatch after treatment with a formulation of the present invention.

Decontamination of a Carpet Swatch Contaminated with VX Surrogate and Additional Material Compatibility Testing Dem-S was selected as the VX surrogate with which to spike the carpet swatches. Two carpet swatches of identical size (2½ inches×2½ inches) were each spiked with 27 $\mu$L Dem-S to provide a contamination level equivalent to 80 lethal percutaneous doses of VX per square foot of carpet. One swatch was treated with 25 mL of decontaminating gel (0.9 M $H_2O_2$, 0.1 M OXONE, 0.09 M $FeSO_4$ and 6 wt % gel) for 5 minutes and the other was untreated. Dem-S was recovered from each swatch and analyzed by liquid chromatograph. FIG. 6 reveals the extent of the decontamination. The chromatogram for the untreated swatch reveals that the Dem-S extracted from the untreated carpet elutes at about 9.7 minutes. (Approximately 85% of the Dem-S was recovered from the untreated carpet swatch when compared to Dem-S standards.) The chromatogram from the extract of the decontamination gel treated carpet shows that greater than 99.5% of the recovered Dem-S was destroyed by the decontamination gel.

After the treated swatch was extracted and a sample of the extract was injected into the liquid chromatograph system, the swatch was washed with 25 mL of water to remove the gel. Close examination of the treated swatch revealed that spots in the carpet that may have once been white were slightly yellow as a result of the iron oxide (rust) formed during the decontamination process. However, subsequent washing with water removed virtually all of the yellowish color. A similar washing process can certainly be accomplished in the real world with a commercial carpet cleaner.

Example 15

Two mL of decontaminating gel (oxidant concentrations of 1 M $H_2O_2$ and 0.1 M OXONE) was placed on the surface of one drywall coupon. The gel was allowed to remain on the coupon overnight. The following day, the dried gel was wiped from the surface of the painted dry-wall coupon with a damp cloth and visually inspected for damage as compared to an untreated coupon. It was clearly difficult to tell the two coupons apart.

In addition to the carpet and painted dry-wall, pieces of concrete and aluminum coupons were also exposed to the gel with no noticeable damage and/or discoloration.

Example 16

Application Method and Spray Testing

Figure 7:
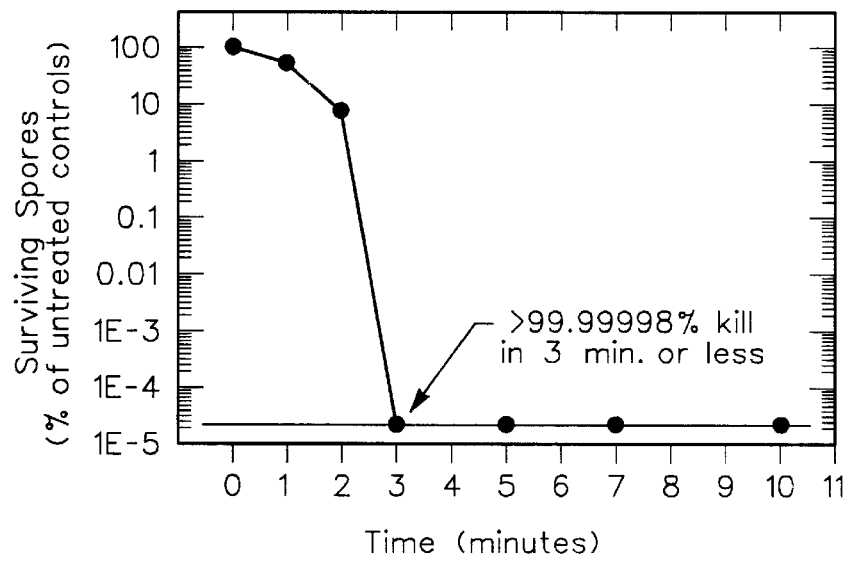
FIG. 7 is a graph showing spore destruction after treatment with a formulation of the present invention.

*Bacillus subtilus* spores were heat fixed onto glass slides and affixed to a large outdoor wall. All the components of the gel were mixed and quickly poured into a 2.5 gal water fire extinguisher fitted with a garden hose nozzle. Once the vessel was pressurized to 100 psi, the premixed gel was dispensed through the nozzle and onto the wall on which the spore coated slides were affixed from a distance of about 15 feet. The results from this spray demonstration are presented in FIG. 7.

The gel dispensed from the vessel, through the nozzle, and onto the contaminated wall reduced the spore count to undetectable levels in 3 minutes. The observation that spore destruction starts off slowly is a phenomena commonly observed with ozone destruction of spores and most likely represents a delay associated with spore coat penetration.

Conclusions

1. The Decontaminating Gel is Universal

Six surrogates representing the three major classes of chemical warfare agents were successfully destroyed by the gel formulation. The gel was also effective at rapidly deactivating *Bacillus subtilus* spores, a surrogate for anthrax. Bacterial endospores are known to be the most resistant life forms to chemical decontaminates. They are used as standard test biological indicators for validation of sterilization/disinfection procedures by medical device manufacturers. The ability to deactivate spores indicates a biocide's ability to kill all known microorganisms.

The oxidative destruction of HD and VX under acidic conditions has been previously reported, but those same conditions failed to effectively destroy G-agents. The formulations of the present invention demonstrate that a combination of oxidants can destroy, surrogates of all three major chemical classes and bacterial endospores.

2. The Combination of Catalyzed or Activated $H_2O_2$ and OXONE Work Synergistically The results of the experiments demonstrate that the combination of catalyzed or activated peroxide and OXONE work better than either oxidant alone. The combination of oxidants resulted in a rapid destruction of CEES and all detectable by-products. Since the hydroxyl radicals generated in the gel formulation are potent and indiscriminate oxidizing agents, it is probable that by-products of other agents are also rapidly destroyed. In addition, the combination of oxidants resulted in a level and rate of spore decontamination better than either oxidant alone and comparable to hypochlorite, a highly effective spore decontaminant.

3. The Concentration of Oxidant in the Gel Formulation

In most of the decontamination experiments performed, the concentration of peroxide in the gel was 0.9 M or 3.1 wt % which is equivalent to the over-the-counter solution used for topical disinfection and mouthwash. In a few examples, gels containing higher oxidant concentrations were used only because of GC/MS detection limits. In addition, this mild gel formulation was successful at decontaminating surrogates at concentrations similar to those encountered in battle field scenarios.

Based on the information obtained from the Examples, Table 2 was prepared to demonstrate the decontamination potential of 10 L of gel versus six current chemical and biological warfare agent threats. The amount of surrogate successfully decontaminated was converted to minimum decontamination potential of chemical and biological warfare agents. The decontamination potential of 10 L of gel is expressed in quantity of agent and number of lethal doses decontaminated.

It is estimated that 10 L of the decontaminating gel can coat 10 m² (100 ft²) of surface with a 1 mm thick gel. Assuming the distribution of the agent is uniform on the surface, 10 L of gel can decontaminate 100 ft² of surface contaminated with 43 lethal percutaneous doses of VX per square foot.

TABLE 2

The decontaminating gel is estimated to be very effective against six major chemical/biological warfare threats.

| Agent | Minimum Decontamination Potential of 10 L of Standard Gel | Lethal Dose of Agent | Number of Lethal Doses 10 L of Gel can Decontaminate |
|---|---|---|---|
| HD | 32 g | 4.48 g[a] | 7 |
| Tabun | 16 g | 1.61 g[a] | 10 |
| Sarin | 14 g | 1.96 g[a] | 7 |
| Soman | 18 g | 1.26 g[a] | 14 |
| VX | 26 g | 6 mg[a] | 4300 |
| anthrax spores | 2.5 mg | ~1 μg[b] | 2500 |

[a]percutaneous;
[b]inhalation

4. Refining the Catalyzed or Activated Peroxide Reaction

The production of hydroxyl radicals from hydrogen peroxide is an exothermic reaction. When the concentrations of peroxide are low (less than 1 M), the heat generated is hardly detectable by touch. However, at higher peroxide concentrations, the temperature of the catalyzed or activated peroxide solution can become quite warm and even hot if the peroxide concentration is high enough. Including phosphate ions in the catalyzed or activated peroxide solution has been found to considerably reduce the temperature of the solution, without reducing the oxidation potential of the solution. Phosphate ion is a known masking agent for $Fe^{3+}$ and stabilizer of $H_2O_2$; either or both of these characteristics may be involved in the observed phenomena. In experiments in which the peroxide concentration in solution exceeded 1 M, phosphate was included to control the temperature of the reaction.

5. Storing and Dispensing the Gel Formulation

The final consideration regarding the decontaminating gel is storage and dispensing. Ideally, the decontaminating gel is stored in two separate reservoirs until needed. Preferably, one reservoir contains the oxidants in a gel and the other reservoir contains the ferrous salt in a gel. When needed, the gels are forced out of their respective containers, into a mixing chamber, out of an appropriate nozzle and onto the surface to be decontaminated. The gels could be forced out either by pressurizing the reservoirs or by pumping the gels from the reservoirs.

A possible challenge to this delivery system is stabilizing the iron as $Fe^{2+}$ and preventing oxidation to $Fe^{3+}$ in a gel formulation. One alternative includes, deoxygenating the iron gel before storage or storing the ferrous salt as a dry material until needed.

While the foregoing is directed to the preferred embodiment of the present invention, other and further embodiments of the invention may be devised without departing from the basic scope thereof, and the scope thereof is determined by the claims which follow.

What is claimed is:

1. A universal decontamination formulation for decomposing toxic chemicals or inactivating harmful biological materials, consisting essentially of:

(a) one or more oxidants, water and a sorbent material, wherein the one or more oxidants, water and the sorbent material have the consistency of a gel, and flyer wherein the gel is stored in a first container; and (b) one or more activating species, water and a sorbent material, wherein the one or more activating species, water and the sorbent material have the consistency of a gel, and further wherein the gel is stored in a second container.

2. The formulation of claim 1, wherein the one or more oxidants is selected from the group consisting of potassium monopersulfate, sodium monopersulfate, ammonium monopersulfate, $HSO_5^-$ salts of alkali metals, $HSO_5^-$ salts of alkaline earth metals, alkali and alkaline earth metal salts of perborates, alkali and alkaline earth metal salts of persulfates, alkali metal peroxides, alkali metal superoxides, alkaline earth metal peroxides and mixtures thereof.

3. The formulation of claim 1, wherein the one or more oxidants comprises $2KHSO_5 \cdot KHSO_4 \cdot K_2SO_4$.

4. The formulation of claim 1, wherein the one or more oxidants is hydrogen peroxide.

5. The formulation of claim 1, wherein the one or more activating species is selected from the group consisting of finely divided metals capable of being readily oxidized to form metal cations, iron salts, iron hydroxides, iron oxyhydroxides, iron oxides, and salts of copper, titanium, chromium, vanadium, zinc, cobalt, nickel and mixtures thereof.

6. The formulation of claim 1, wherein the one or more activating species is a ferrous salt.

7. The formulation of claim 1, wherein the one or more activating species is ferrous sulfate.

8. The formulation of claim 1, further comprising phosphate ions.

9. The formulation of claim 1, wherein the sorbent material is selected from the group consisting of silicon oxide, silica gel, silicon oxyhydroxides, aluminum oxide, titanium oxide, alumina gel, aluminum oxyhydroxides, aluminates and mixtures thereof.

10. The formulation of claim 1, wherein the sorbent material is fumed silica.

11. The formulation of claim 3, wherein the one or more oxidants provide an $HSO_5^-$ ion concentration of from about 0.05M to about 0.5M.

12. The formulation of claim 3, wherein the one or more oxidants provide an $HSO_5^-$ ion concentration of from about 0.1M to about 0.3M.

13. The formulation of claim 1, wherein the concentration of the one or more oxidants is from about 0.5M to about 5M.

14. The formulation of claim 1, wherein the concentration of the one or more oxidants is from about 0.5M to about 1.5M.

15. The formulation of claim 1, wherein the concentration of the one or more activating species is from about 0.05M to about 0.5M.

16. The formulation of claim 1, wherein the concentration of the one or more activating species is from about 0.1M to about 0.3M.

17. The formulation of claim 10, wherein the sorbent material concentration is from about 3 wt % to about 20 wt %.

18. The formulation of claim 10, wherein the sorbent material concentration is from about 5 wt % to about 15 wt %.

19. The formulation of claim 1, wherein the two components are mixed together intimately during the act of being applied to a surface.

20. The universal decontamination formulation of claim 1, wherein the toxic chemicals comprise chemical warfare agents and pesticides.

21. The universal decontamination formulation of claim 1, wherein the harmful biological materials comprise biological warfare agents.

22. The universal decontamination formulation of claim 20, wherein the chemical warfare agents are selected from mustards, and organophosphorous nerve agents of the G type and V type, and combinations thereof.

23. The formulation of claim 21, wherein the biological materials are selected from viruses, bacteria, rickettsia, biological toxins, genetically engineered agents, and combinations thereof.

24. The universal decontamination formulation of claim 1, wherein activation of the oxidant by the activating species produces hydroxyl radicals.

25. The formulation of claim 1, wherein there is sorption of a toxic chemical or harmful biological material into the gel.

26. The formulation of claim 1, wherein the first container, or the second container or both the first and second containers contain a source of phosphate ions.

27. The formulation of claim 1, wherein the first and second gels are forced out of the first and second containers, through a mixing chamber, out of a nozzle, and onto a surface to be decontaminated.

28. The formulation of claim 1, wherein the sorbent material has a concentration ranging from about 3% to about 20% by weight of the formulation.

29. The formulation of claim 1, wherein the sorbent material has a concentration ranging from about 5% to about 15% by weight of the formulation.

30. The formulation of claim 1, wherein the first and second containers are first and second chambers of a common container.

31. The formulation of claim 1, wherein the first and second containers are formed in a common or different containers.

32. The formulation of claim 1, wherein the one or more oxidants are selected from hydrogen peroxide, $2KHSO_5 \cdot KHSO_4 \cdot K_2SO_4$, and combinations thereof.

33. A universal decontamination formulation having the consistency of a gel for decomposing toxic chemicals or inactivating harmful biological materials, consisting essentially of:
water as a solvent;
an oxidant;
a source of phosphate ions;
an activating species for the oxidant; and
an inert sorbent material.

34. The universal decontamination formulation of claim 33, wherein the oxidant is selected from the group consisting of potassium monopersulfate, sodium monopersulfate, ammonium monopersulfate, $HSO_5^-$ salts of alkali metals, $HSO_5^-$ salts of alkaline earth metals, alkali and alkaline earth metal salts of perborates, alkali and alkaline earth metal salts of persulfates, alkali metal peroxides, alkali metal superoxides, alkaline earth metal peroxides and mixtures thereof.

35. The universal decontamination formulation of claim 33, wherein the oxidant is selected from hydrogen peroxide, $2KHSO_5 \cdot KHSO_4 \cdot K_2SO_4$, and combinations thereof.

36. The universal decontamination formulation of claim 33, wherein the oxidant is hydrogen peroxide.

37. The universal decontamination formulation of claim 33, wherein the inert sorbent material absorbs toxic agents into the sorbent containing the oxidant and the activating species.

38. The universal decontamination formulation of claim 37, wherein the inert sorbent is fumed silica.

39. The universal decontamination formulation of claim 33, wherein the inert sorbent material is in the gel state.

40. The universal decontamination formulation of claim 33, wherein the activating species is selected from the group consisting of finely divided metals capable of being readily oxidized to form metal cations, iron salts, iron hydroxides, iron oxyhydroxides, iron oxides, and salts of copper, titanium, chromium, vanadium, zinc, cobalt, nickel and mixtures thereof.

41. The universal decontamination formulation of claim 33, wherein the activating species is a ferrous salt.

42. The universal decontamination formulation of claim 33, wherein the activating species is ferrous sulfate.

43. The universal decontamination formulation of claim 33, wherein the sorbent material is selected from the group consisting of silicon oxide, silica gel, silicon oxyhydroxides, aluminum oxide, titanium oxide, alumina gel, aluminum oxyhydroxides, aluminates and mixtures thereof.

44. The universal decontamination formulation of claim 33, wherein activation of the oxidant by the activating species produces hydroxyl radicals.

45. The formulation of claim 33, wherein the oxidant includes hydrogen peroxide and $2KHSO_5 \cdot KHSO_4 \cdot K_2SO_4$.

46. A chemical composition for decomposing toxic chemicals or inactivating harmful biological materials, the chemical composition consisting essentially of:
    (a) a first gel material having one or more oxidants, water and a sorbent;
    (b) a second gel material having one or more activating species, water and a sorbent.

47. The chemical composition of claim 45, wherein the first or second gels are formed from a sorbent material having a surface area of about 200 $m^2 g^{-1}$.

48. The chemical composition of claim 45, wherein the first gel further comprises a source of phosphate ions.

49. The chemical composition of claim 45, wherein the chemical composition is stored in two separate reservoirs within a container, or in two separate containers.

50. The chemical composition of claim 49, wherein one reservoir within the container, or the first container, contains the oxidants in a gel and the other reservoir within the container, or the second container contains the activating species in a gel.

51. The chemical composition of claim 46, wherein the one or more oxidants is selected from the group consisting of potassium monopersulfate, sodium monopersulfate, ammonium monopersulfate, $HSO_5^-$ salts of alkali metals, $HSO_5^-$ salts of alkaline earth metals, alkali and alkaline earth metal salts of perborates, alkali and alkaline earth metal salts of persulfates, alkali metal peroxides, alkali metal superoxides, alkaline earth metal peroxides and mixtures thereof.

52. The chemical composition of claim 46, wherein the one or more oxidants comprises $2KHSO_5 \cdot KHSO_4 \cdot K_2SO_4$.

53. The chemical composition of claim 46, wherein the one or more oxidants is hydrogen peroxide.

54. The chemical composition of claim 46, wherein the one or more activating species is selected from the group consisting of finely divided metals capable of being readily oxidized to form metal cations, iron salts, iron hydroxides, iron oxyhydroxides, iron oxides, and salts of copper, titanium, chromium, vanadium, zinc, cobalt, nickel and mixtures thereof.

55. The chemical composition of claim 46, wherein the one or more activating species is a ferrous salt.

56. The chemical composition of claim 46, wherein the one or more activating species is a ferrous sulfate.

57. The chemical composition of claim 46, wherein the sorbent material is selected from the group consisting of silicon oxide, silica gel, silicon oxyhydroxides, aluminum oxide, titanium oxide, alumina gel, aluminum oxyhydroxides, aluminates and mixtures thereof.

58. The chemical composition of claim 46, wherein the sorbent material is fumed silica.

59. The chemical composition of claim 46, wherein the two gels are mixed together intimately during the act of being applied to a surface.

60. A universal decontamination formulation for decomposing toxic chemicals or inactivating harmful biological materials, consisting essentially of:
    (a) an aqueous solution of one or more oxidants; and
    (b) a gel material comprising one or more activating species, water and a sorbent material.

61. The formulation of claim 60, wherein the one or more oxidants is selected from the group consisting of potassium monopersulfate, sodium monopersulfate, ammonium monopersulfate, $HSO_5^-$ salts of alkali metals, $HSO_5^-$ salts of alkaline earth metals, alkali and alkaline earth metal salts of perborates, alkali and alkaline earth metal salts of persulfates, alkali metal peroxides, alkali metal superoxides, alkaline earth metal peroxides and mixtures thereof.

62. The formulation of claim 60, wherein the one or more oxidants comprises $2KHSO_5 \cdot KHSO_4 \cdot K_2SO_4$.

63. The formulation of claim 60, wherein the one or more oxidants is hydrogen peroxide.

64. The formulation of claim 60, wherein the one or more activating species is selected from the group consisting of finely divided metals capable of being readily oxidized to form metal cations, iron salts, iron hydroxides, iron oxyhydroxides, iron oxides, and salts of copper, titanium, chromium, vanadium, zinc, cobalt, nickel and mixtures thereof.

65. The formulation of claim 60, wherein the one or more activating species is a ferrous salt.

66. The formulation of claim 60, wherein the sorbent material is fumed silica.

67. The formulation of claim 66, wherein the aqueous solution and the gel are mixed together intimately during the act of being applied to a surface.

68. The formulation of claim 60, wherein the one or more activating species is ferrous sulfate.

69. The formulation of claim 60, father comprising phosphate ions.

70. The formulation of claim 60, wherein the sorbent material is selected from the group consisting of silicon oxide, silica gel, silicon oxyhydroxides, aluminum oxide, titanium oxide, alumina gel, aluminum oxyhydroxides, aluminates and mixtures thereof.

71. A universal decontamination formulation for decomposing toxic chemicals or inactivating harmful biological materials, consisting essentially of:
one or more oxidants, one or more activating species, one or more sorbent materials, and water, wherein the one or more oxidants, one or more activating species, one or more sorbent materials and water have the consistency of a gel.

72. The formulation of claim 71, wherein the sorbent material comprises between 3 and 20 weight percent of the formulation.

73. The formulation of claim 71, wherein the sorbent material comprises between 5 and 15 weight percent of the formulation.

74. The formulation of claim 71, wherein the one or more oxidants is selected from the group consisting of potassium monopersulfate, sodium monopersulfate, ammonium monopersulfate, $HSO_5^-$ salts of alkali metals, $HSO_5^-$ salts of alkaline earth metals, alkali and alkaline earth metal salts of perborates, alkali and alkaline earth metal salts of persulfates, alkali metal peroxides, alkali metal superoxides, alkaline earth metal peroxides and mixtures thereof.

75. The formulation of claim 71, wherein the one or more oxidants comprises $2KHSO_5 \cdot KHSO_4 \cdot K_2SO_4$.

76. The formulation of claim 71, wherein the one or more oxidants is hydrogen peroxide.

77. The formulation of claim 71, wherein the one or more activating species is selected from the group consisting of finely divided metals capable of being readily oxidized to form metal cations, iron salts, iron hydroxides, iron oxyhydroxides, iron oxides, and salts of copper, titanium, chromium, vanadium, zinc, cobalt, nickel and mixtures thereof.

78. The formulation of claim 71, wherein the one or more activating species is a ferrous salt.

79. The formulation of claim 71, wherein the one or more activating species is ferrous sulfate.

80. The formulation of claim 71, wherein the one or more sorbent materials are selected from the group consisting of silicon oxide, silica gel, silicon oxyhydroxides, aluminum oxide, titanium oxide, alumina gel, aluminum oxyhydroxides, aluminates and mixtures thereof.

81. The formulation of claim 71, wherein the one or more sorbent materials is fumed silica.

82. The formulation of claim 71, further comprising phosphate ions.

83. A universal decontamination formulation for decomposing toxic chemicals or inactivating harmful biological materials, comprising:
one or more oxidants, water and a sorbent material, wherein the one or more oxidants, water and the sorbent material have the consistency of a gel, and further wherein the gel is stored in a first container; and
one or more activating species, water and a sorbent material, wherein the one or more activating species, water and the sorbent material have the consistency of a gel, further wherein the gel is stored in a second container, and wherein the formulation is essentially free of organic material.

84. The formulation of claim 83, wherein the one or more oxidants is selected from the group consisting of potassium monopersulfate, sodium monopersulfate, ammonium monopersulfate, $HSO_5^-$ salts of alkali metals, $HSO_5^-$ salts of alkaline earth metals, alkali and alkaline earth metal salts of perborates, alkali and alkaline earth metal salts of persulfates, alkali metal peroxides, alkali metal superoxides, alkaline earth metal peroxides and mixtures thereof.

85. The formulation of claim 83, wherein the one or more oxidants comprises $2KHSO_5 \cdot KHSO_4 \cdot K_2SO_4$.

86. The formulation of claim 83, wherein the one or more oxidants is hydrogen peroxide.

87. The formulation of claim 83, wherein the one or more activating species is selected from the group consisting of finely divided metals capable of being readily oxidized to form metal cations, iron salts, iron hydroxides, iron oxyhydroxides, iron oxides, and salts of copper, titanium, chromium, vanadium, zinc, cobalt, nickel and mixtures thereof.

88. The formulation of claim 83, wherein the one or more activating species is a ferrous salt.

89. The formulation of clam 83, wherein the one or more activating species is ferrous sulfate.

90. The formulation of claim 83, further comprising phosphate ions.

91. The formulation of claim 83, wherein the sorbent material is selected from the group consisting of silicon oxide, silica gel, silicon oxyhydroxides, aluminum oxide, titanium oxide, alumina gel, aluminum oxyhydroxides, aluminates and mixtures thereof.

92. The formulation of claim 83, wherein the sorbent material is fumed silica.

93. The formulation of claim 85, wherein the one or more oxidants provide an $HSO_5^-$ ion concentration of from about 0.05M to about 0.5M.

94. The formulation of claim 85, wherein the one or more oxidants provide an $HSO_5^-$ ion concentration of from about 0.1M to about 0.3M.

95. The formulation of claim 83, wherein the concentration of the one or more oxidants is from about 0.5M to about 5M.

96. The formulation of claim 83, wherein the concentration of the one or more oxidants is from about 0.5M to about 1.5M.

97. The formulation of claim 83, wherein the concentration of the one or more activating species is from about 0.05M to about 0.5M.

98. The formulation of claim 83, wherein the concentration of the one or more activating species is from about 0.1M to about 0.3M.

99. The formulation of claim 83, wherein the sorbent material concentration is from between about 3 wt % to about 20 wt %.

100. The formulation of claim 83, wherein the sorbent material concentration is from between about 5 wt % to about 15 wt %.

101. The formulation of claim 83, wherein the two components are mixed together intimately during the act of being applied to a surface.

102. The formulation of claim 83, wherein the toxic chemicals comprise chemical warfare agents and pesticides.

103. The formulation of claim 83, wherein the harmful biological materials comprise biological warfare agents.

104. The formulation of claim 102, wherein the chemical warfare agents are selected from mustards, and organophosphorous nerve agents of the G type and V type, and combinations thereof.

105. The formulation of claim 103, wherein the biological materials are selected from viruses, bacteria, rickettsia, biological toxins, genetically engineered agents, and combinations thereof.

106. The formulation of claim 83, wherein activation of the oxidant by the activating species produces hydroxyl radicals.

107. The formulation of claim 83, wherein there is sorption of a toxic chemical or harmful biological material into the gel.

108. The formulation of claim 83, wherein the first container, or the second container or both the first and second containers contain a source of phosphate ions.

109. The formulation of claim 83, wherein the first and second gels are forced out of the first and second containers, through a mixing chamber, out of a nozzle, and onto a surface to be decontaminated.

110. The formulation of claim 83, wherein the first and second continers are formed in a common or different containers.

111. A universal decontamination formulation having the consistency of a gel for decomposing toxic chemicals or inactivating harmful biological materials, comprising:
   water as a solvent;
   an oxidant;
   a source of phosphate ions;
   an activating species for the oxidant; and
   an inert sorbent material, wherein the formulation is essentially free of organic material.

112. The formulation of claim 111, wherein the oxidant is selected from the group consisting of potassium monopersulfate, sodium monopersulfate, ammonium monopersulfate, $HSO_5^-$ salts of alkali metals, $HSO_5^-$ salts of alkaline earth metals, alkali and alkaline earth metal salts of perborates, alkali and alkaline earth metal salts of persulfates, alkali metal peroxides, alkali metal superoxides, alkaline earth metal peroxides and mixtures thereof.

113. The formulation of claim 111, wherein the oxidant comprises $2KHSO_5.KHSO_4.K_2SO_4$.

114. The formulation of claim 111, wherein the oxidant is hydrogen peroxide.

115. The formulation of claim 111, wherein the activating species is selected from the group consisting of finely divided metals capable of being readily oxidized to form metal cations, iron salts, iron hydroxides, iron oxyhydroxides, iron oxides, and salts of copper, titanium, chromium, vanadium, zinc, cobalt, nickel and mixtures thereof.

116. The formulation of claim 111, wherein the activating species is a ferrous salt.

117. The formulation of claim 111, wherein the activating species is ferrous sulfate.

118. The formulation of claim 111, wherein the sorbent material is selected from the group consisting of silicon oxide, silica gel, silicon oxyhydroxides, aluminum oxide, titanium oxide, alumina gel, aluminum oxyhydroxides, aluminates and mixtures thereof.

119. The formulation of claim 111, wherein the sorbent material is fumed silica.

120. The formulation of claim 113, wherein the oxidant provides an $HSO_5^-$ ion concentration of from about 0.05M to about 0.5M.

121. The formulation of claim 113, wherein the oxidant provides an $HSO_5^-$ ion concentration of from about 0.1M to about 0.3M.

122. The formulation of claim 111, wherein the concentration of the oxidant is from about 0.5M to about 5M.

123. The formulation of claim 111, wherein the concentration of the oxidant is from about 0.5M to about 1.5M.

124. The formulation of claim 111, wherein the concentration of the activating species is from about 0.05M to about 0.5M.

125. The formulation of claim 111, wherein the concentration of the activating species is from about 0.1M to about 0.3M.

126. The formulation of claim 111, wherein the sorbent material concentration is from between about 3 wt % to about 20 wt %.

127. The formulation of claim 111, wherein the sorbent material concentration is from between about 5 wt % to about 15 wt %.

128. The formulation of claim 111, wherein the toxic chemicals comprise chemical warfare agents and pesticides.

129. The formulation of claim 111, wherein the harmful biological materials comprise biological warfare agents.

130. The formulation of claim 128, wherein the chemical warfare agents are selected from mustards, and organophosphorous nerve agents of the G type and V type, and combinations thereof.

131. The formulation of claim 129, wherein the biological materials are selected from viruses, bacteria, rickettsia, biological toxins, genetically engineered agents, and combinations thereof.

132. The formulation of claim 111, wherein activation of the oxidant by the activating species produces hydroxyl radicals.

133. The formulation of claim 111, wherein there is sorption of a toxic chemical or harmful biological material into the gel.

134. A universal decontamination formulation for decomposing toxic chemicals or inactivating harmful biological materials, comprising:
   an aqueous solution of one or more oxidants; and
   a gel material comprising one or more activating species, water and a sorbent material, wherein the formulation is essentially free of organic material.

135. The formulation of claim 134, wherein the one or more oxidants is selected from the group consisting of potassium monopersulfate, sodium monopersulfate, ammonium monopersulfate, $HSO_5^-$ salts of alkali metals, $HSO_5^-$ salts of alkaline earth metals, alkali and alkaline earth metal salts of perborates, alkali and alkaline earth metal salts of persulfates, alkali metal peroxides, alkali metal superoxides, alkaline earth metal peroxides and mixtures thereof.

136. The formulation of claim 134, wherein the one or more oxidants comprises $2KHSO_5.KHSO_4.K_2SO_4$.

137. The formulation of claim 134, wherein the one or more oxidants is hydrogen peroxide.

138. The formulation of claim 134, wherein the one or more activating species is selected from the group consisting of finely divided metals capable of being readily oxidized to form metal cations, iron salts, iron hydroxides, iron oxyhydroxides, iron oxides, and salts of copper, titanium, chromium, vanadium, zinc, cobalt, nickel and mixtures thereof.

139. The formulation of claim 134, wherein the one or more activating species is a ferrous salt.

140. The formulation of claim 134, wherein the one or more activating species is ferrous sulfate.

141. The formulation of claim 134, further comprising phosphate ions.

142. The formulation of claim 134, wherein the sorbent material is selected from the group consisting of silicon oxide, silica gel, silicon oxyhydroxides, aluminum oxide, titanium oxide, alumina gel, aluminum oxyhydroxides, aluminates and mixtures thereof.

143. The formulation of claim 134, wherein the sorbent material is fumed silica.

144. The formulation of claim 136, wherein the one or more oxidants provide an $HSO_5^-$ ion concentration of from about 0.05M to about 0.5M.

145. The formulation of claim 136, wherein the one or more oxidants provide an $HSO_5^-$ ion concentration of from about 0.1M to about 0.3M.

146. The formulation of claim 134, wherein the concentration of the one or more oxidants is from about 0.5M to about 5M.

147. The formulation of claim 134, wherein the concentration of the one or more oxidants is from about 0.5M to about 1.5M.

148. The formulation of claim 134, wherein the concentration of the one or more activating species is from about 0.05M to about 0.5M.

149. The formulation of claim 134, wherein the concentration of the one or more activating species is from about 0.1M to about 0.3M.

150. The formulation of claim 134, wherein the sorbent material concentration is from between about 3 wt % to about 20 wt %.

151. The formulation of claim 134, wherein the sorbent material concentration is from between about 5 wt % to about 15 wt %.

152. The formulation of claim 134, wherein activation of the oxidant by the activating species produces hydroxyl radicals.

153. The formulation of claim 134, wherein there is sorption of a toxic chemical or harmful biological material into the gel.

154. A universal decontamination formulation for decomposing toxic chemicals or inactivating harmful biological materials, comprising:
one or more oxidants, one or more activating species, one or more sorbent materials, and water, wherein the one or more oxidants, one or more activating species, one or more sorbent materials and water have the consistency of a gel, and wherein the formulation is essentially free of organic material.

155. The formulation of claim 154, wherein the one or more oxidants is selected from the group consisting of potassium monopersulfate, sodium monopersulfate, ammonium monopersulfate, $HSO_5^-$ salts of alkali metals, $HSO_5^-$ salts of alkaline earth metals, alkali and alkaline earth metal salts of perborates, alkali and alkaline earth metal salts of persulfates, alkali metal peroxides, alkali metal superoxides, alkaline earth metal peroxides and mixtures thereof.

156. The formulation of claim 151, wherein the one or more oxidants comprises $2KHSO_5 \cdot KHSO_4 \cdot K_2SO_4$.

157. The formulation of claim 151, wherein the one or more oxidants is hydrogen peroxide.

158. The formulation of claim 151, wherein the one or more activating species is selected from the group consisting of finely divided metals capable of being readily oxidized to form metal cations, iron salts, iron hydroxides, iron oxyhydroxides, iron oxides, and salts of copper, titanium, chromium, vanadium, zinc, cobalt, nickel and mixtures thereof.

159. The formulation of claim 151, wherein the one or more activating species is a ferrous salt.

160. The formulation of claim 151, wherein the one or more activating species is ferrous sulfate.

161. The formulation of claim 151, further comprising phosphate ions.

162. The formulation of claim 151, wherein the one or more sorbent materials are selected from the group consisting of silicon oxide, silica gel, silicon oxyhydroxides, aluminum oxide, titanium oxide, alumina gel, aluminum oxyhydroxides, aluminates and mixtures thereof.

163. The formulation of claim 151, wherein the one or more sorbent materials is fumed silica.

164. The formulation of claim 156, wherein the one or more oxidants provide an $HSO_5^-$ ion concentration of from about 0.05M to about 0.5M.

165. The formulation of claim 156, wherein the one or more oxidants provide an $HSO_5^-$ ion concentration of from about 0.1M to about 0.3M.

166. The formulation of claim 151, wherein the concentration of the one or more oxidants is from about 0.5M to about 5M.

167. The formulation of claim 151, wherein the concentration of the one or more oxidants is from about 0.5M to about 1.5M.

168. The formulation of claim 151, wherein the concentration of the one or more activating species is from about 0.05M to about 0.5M.

169. The formulation of claim 151, wherein the concentration of the one or more activating species is from about 0.1M to about 0.3M.

170. The formulation of claim 151, wherein the one or more sorbent materials concentration is from between about 3 wt % to about 20 wt %.

171. The formulation of claim 151, wherein the one or more sorbent materials concentration is from between about 5 wt % to about 15 wt %.

172. The formulation of claim 151, wherein activation of the oxidant by the activating species produces hydroxyl radicals.

173. The formulation of claim 151, wherein there is sorption of a toxic chemical or harmful biological material into the gel.

174. The formulation of claim 1, characterized in that the one or more oxidants is dispersible in the one or more activating species.

* * * * *